US009427339B2

(12) United States Patent
Shalev

(10) Patent No.: US 9,427,339 B2
(45) Date of Patent: Aug. 30, 2016

(54) TRIPLE-COLLAR STENT-GRAFT

(71) Applicant: ENDOSPAN LTD., Herzilyia Pituach (IL)

(72) Inventor: Alon Shalev, Ra'anana (IL)

(73) Assignee: ENDOSPAN LTD., Herzilyia Pituach (IL)

( * ) Notice: Subject to any disclaimer, the term of this patent is extended or adjusted under 35 U.S.C. 154(b) by 316 days.

(21) Appl. No.: 14/355,438

(22) PCT Filed: Oct. 29, 2012

(86) PCT No.: PCT/IL2012/050424
§ 371 (c)(1),
(2) Date: Apr. 30, 2014

(87) PCT Pub. No.: WO2013/065040
PCT Pub. Date: May 10, 2013

(65) Prior Publication Data
US 2014/0288635 A1 Sep. 25, 2014

Related U.S. Application Data

(60) Provisional application No. 61/553,209, filed on Oct. 30, 2011.

(51) Int. Cl.
*A61F 2/06* (2013.01)
*A61F 2/82* (2013.01)
(Continued)

(52) U.S. Cl.
CPC . *A61F 2/82* (2013.01); *A61F 2/07* (2013.01); *A61F 2/89* (2013.01); *A61F 2/90* (2013.01);
(Continued)

(58) Field of Classification Search
CPC ............... A61F 2210/0057; A61F 2210/0066; A61F 2250/0007; A61F 2/07
See application file for complete search history.

(56) References Cited

U.S. PATENT DOCUMENTS 4,180,613 A 12/1979 Vassiliou
4,355,426 A 10/1982 MacGregor
(Continued)

FOREIGN PATENT DOCUMENTS

CA 2497704 3/2004
CN 2453960 10/2001
(Continued)

OTHER PUBLICATIONS

An Office Action dated Oct. 2, 2015, which issued during the prosecution of U.S. Appl. No. 13/577,161.
(Continued)

*Primary Examiner* — Gregory Anderson
(74) *Attorney, Agent, or Firm* — Sughrue Mion, PLLC

(57) ABSTRACT

An endovascular stent-graft (20, 120, 180, 220, 320) includes a fluid flow guide (22), and a plurality of structural stent elements (24) attached to at least a portion of the fluid flow guide (22). The stent-graft is configured to define a generally tubular foldable section (30), which comprises first, second, and third subsections (32, 34, 36). The stent-graft is configured to assume a delivery configuration and a deployment configuration. In the delivery configuration, (a) the stent-graft, including the foldable section (30), is in a radially-compressed state, and (b) the foldable section (30) is in a longitudinally-expanded state, in which state the first and the third subsections (32, 36) longitudinally surround the second subsection (34). In the deployment configuration, (a) the stent-graft, including the foldable section (30), is in a radially-expanded state, and (b) the foldable section (30) is in a longitudinally-folded state, such that the second subsection (34) is radially sandwiched between the first and the third subsections (32, 36). Other embodiments are also described.

26 Claims, 11 Drawing Sheets

(51) Int. Cl.
*A61F 2/07* (2013.01)
*A61F 2/966* (2013.01)
*A61F 2/89* (2013.01)
*A61F 2/90* (2013.01)

(52) U.S. Cl.
CPC .......... *A61F 2/966* (2013.01); *A61F 2002/061* (2013.01); *A61F 2002/075* (2013.01); *A61F 2250/006* (2013.01)

(56) References Cited

U.S. PATENT DOCUMENTS

| | | |
|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,133,732 A | 7/1992 | Wiktor |
| 5,192,256 A | 3/1993 | Ryan |
| 5,192,286 A | 3/1993 | Phan et al. |
| 5,234,448 A | 8/1993 | Wholey et al. |
| 5,383,926 A | 1/1995 | Lock et al. |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,575,818 A | 11/1996 | Pinchuk |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,792,172 A | 8/1998 | Fischell et al. |
| 5,824,040 A | 10/1998 | Cox et al. |
| 5,824,055 A | 10/1998 | Spiridigliozzi et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,948,018 A | 9/1999 | Dereume et al. |
| 5,968,091 A | 10/1999 | Pinchuk et al. |
| 5,980,552 A | 11/1999 | Pinchasik et al. |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,723 A | 3/2000 | Anidjar et al. |
| 6,036,725 A | 3/2000 | Avellanet |
| 6,049,824 A | 4/2000 | Simonin |
| 6,051,021 A | 4/2000 | Frid |
| 6,059,824 A | 5/2000 | Taheri |
| 6,077,298 A | 6/2000 | Tu et al. |
| 6,099,497 A | 8/2000 | Adams et al. |
| 6,099,548 A | 8/2000 | Taheri |
| 6,117,145 A | 9/2000 | Wood et al. |
| 6,129,738 A | 10/2000 | Lashinski et al. |
| 6,132,457 A | 10/2000 | Chobotov |
| 6,152,956 A | 11/2000 | Pierce |
| 6,156,064 A | 12/2000 | Chouinard |
| 6,159,228 A | 12/2000 | Frid et al. |
| 6,168,615 B1 | 1/2001 | Ken et al. |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 | 9/2001 | Drasler et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,819 B1 | 12/2001 | Pavcnik et al. |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy et al. |
| 6,428,565 B1 | 8/2002 | Wisselink |
| 6,451,051 B2 | 9/2002 | Drasler et al. |
| 6,471,722 B1 | 10/2002 | Inoue |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,576,009 B2 | 6/2003 | Ryan et al. |
| 6,613,078 B1 | 9/2003 | Barone |
| 6,635,083 B1 | 10/2003 | Cheng et al. |
| 6,645,242 B1 | 11/2003 | Quinn |
| 6,648,911 B1 | 11/2003 | Sirhan et al. |
| 6,652,567 B1 | 11/2003 | Deaton |
| 6,652,571 B1 | 11/2003 | White et al. |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,695,875 B2 | 2/2004 | Stelter et al. |
| 6,699,277 B1 | 3/2004 | Freidberg et al. |
| 6,716,238 B2 | 4/2004 | Elliott |
| 6,733,523 B2 | 5/2004 | Shaolian et al. |
| 6,743,195 B2 | 6/2004 | Zucker |
| 6,748,953 B2 | 6/2004 | Sherry et al. |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,953,469 B2 | 10/2005 | Ryan |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |

(56) References Cited

U.S. PATENT DOCUMENTS

| | | |
|---|---|---|
| 7,022,131 B1 | 4/2006 | Derowe et al. |
| 7,044,962 B2 | 5/2006 | Elliott |
| 7,105,015 B2 | 9/2006 | Goshgarian |
| 7,105,020 B2 | 9/2006 | Greenberg et al. |
| 7,112,217 B1 | 9/2006 | Kugler et al. |
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,261,733 B1 | 8/2007 | Brown et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,399,313 B2 | 7/2008 | Brown et al. |
| 7,407,509 B2 | 8/2008 | Greenberg et al. |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,616,997 B2 | 11/2009 | Kieval et al. |
| 7,637,939 B2 | 12/2009 | Tischler |
| 7,645,298 B2 | 1/2010 | Hartley et al. |
| 7,655,036 B2 | 2/2010 | Goodson |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,699,885 B2 | 4/2010 | Leonhardt et al. |
| 7,708,704 B2 | 5/2010 | Mitelberg et al. |
| 7,722,626 B2 | 5/2010 | Middleman et al. |
| 7,731,732 B2 | 6/2010 | Ken |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,178 B2 | 9/2010 | Whirley et al. |
| 7,806,923 B2 | 10/2010 | Moloney |
| 7,815,673 B2 | 10/2010 | Bloom et al. |
| 7,833,259 B2 | 11/2010 | Boatman |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias et al. |
| 8,080,026 B2 | 12/2011 | Konstantino et al. |
| 8,080,053 B2 | 12/2011 | Satasiya et al. |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,167,926 B2 | 5/2012 | Hartley et al. |
| 8,172,892 B2 | 5/2012 | Chuter et al. |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,486,131 B2 | 7/2013 | Shalev |
| 8,491,646 B2 | 7/2013 | Schreck |
| 8,506,622 B2 | 8/2013 | Bruszewski et al. |
| 2001/0000188 A1 | 4/2001 | Lenker et al. |
| 2001/0004705 A1 | 6/2001 | Killion et al. |
| 2001/0014823 A1 | 8/2001 | Ressemann et al. |
| 2001/0034550 A1 | 10/2001 | Buirge et al. |
| 2001/0037142 A1 | 11/2001 | Stelter et al. |
| 2001/0044647 A1 | 11/2001 | Pinchuk et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0052643 A1 | 5/2002 | Wholey et al. |
| 2002/0052644 A1 | 5/2002 | Shaolian et al. |
| 2002/0072790 A1 | 6/2002 | McGuckin, Jr. et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0111667 A1 | 8/2002 | Girton et al. |
| 2002/0123791 A1 | 9/2002 | Harrison |
| 2002/0156495 A1 | 10/2002 | Brenneman et al. |
| 2002/0156517 A1 | 10/2002 | Perouse |
| 2002/0173809 A1 | 11/2002 | Fleischman et al. |
| 2002/0183783 A1 | 12/2002 | Shadduck |
| 2002/0193864 A1 | 12/2002 | Khosravi et al. |
| 2002/0198585 A1 | 12/2002 | Wisselink |
| 2003/0033005 A1 | 2/2003 | Houser et al. |
| 2003/0040791 A1 | 2/2003 | Oktay |
| 2003/0065386 A1 | 4/2003 | Weadock |
| 2003/0068296 A1 | 4/2003 | Ricci et al. |
| 2003/0074055 A1 | 4/2003 | Haverkost |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0144725 A1 | 7/2003 | Lombardi |
| 2003/0153944 A1 | 8/2003 | Phung et al. |
| 2003/0153968 A1 | 8/2003 | Geis et al. |

(56) References Cited

U.S. PATENT DOCUMENTS

| | | |
|---|---|---|
| 2003/0163187 A1 | 8/2003 | Weber |
| 2003/0171771 A1 | 9/2003 | Anderson et al. |
| 2003/0191523 A1 | 10/2003 | Hojeibane |
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0181149 A1 | 9/2004 | Langlotz et al. |
| 2004/0215319 A1 | 10/2004 | Berra et al. |
| 2004/0215320 A1 | 10/2004 | Machek |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0137682 A1 | 6/2005 | Justino |
| 2005/0143802 A1 | 6/2005 | Soykan et al. |
| 2005/0149166 A1 | 7/2005 | Schaeffer et al. |
| 2005/0154448 A1 | 7/2005 | Cully et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0171599 A1 | 8/2005 | White |
| 2005/0177132 A1 | 8/2005 | Lentz et al. |
| 2005/0203606 A1 | 9/2005 | VanCamp |
| 2005/0216018 A1 | 9/2005 | Sennett |
| 2005/0222649 A1 | 10/2005 | Capuano et al. |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095104 A1 | 5/2006 | Magers et al. |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis, Jr. et al. |
| 2006/0173530 A1 | 8/2006 | Das |
| 2006/0190070 A1 | 8/2006 | Dieck et al. |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2007/0016281 A1 | 1/2007 | Melsheimer |
| 2007/0021822 A1 | 1/2007 | Boatman |
| 2007/0027526 A1 | 2/2007 | Demetriades et al. |
| 2007/0043425 A1 | 2/2007 | Hartley et al. |
| 2007/0050011 A1 | 3/2007 | Klein et al. |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Maxime et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Maxime et al. |
| 2007/0168013 A1 | 7/2007 | Douglas |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu et al. |
| 2007/0225797 A1 | 9/2007 | Krivoruhko |
| 2007/0233229 A1 | 10/2007 | Berra et al. |
| 2007/0237973 A1 | 10/2007 | Purdy et al. |
| 2007/0239256 A1 | 10/2007 | Weber et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0033527 A1 | 2/2008 | Nunez et al. |
| 2008/0058918 A1 | 3/2008 | Watson |
| 2008/0064957 A1 | 3/2008 | Spence |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0147173 A1 | 6/2008 | Mciff et al. |
| 2008/0167704 A1 | 7/2008 | Wright et al. |
| 2008/0176271 A1 | 7/2008 | Silver et al. |
| 2008/0195190 A1 | 8/2008 | Bland et al. |
| 2008/0195191 A1 | 8/2008 | Luo et al. |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069881 A1 | 3/2009 | Chalekian et al. |
| 2009/0069882 A1 | 3/2009 | Venturelli et al. |
| 2009/0082841 A1 | 3/2009 | Zacharias et al. |
| 2009/0082847 A1 | 3/2009 | Zacharias et al. |
| 2009/0099647 A1 | 4/2009 | Glimsdale et al. |
| 2009/0099648 A1 | 4/2009 | Yu |

(56) References Cited

U.S. PATENT DOCUMENTS

| | | |
|---|---|---|
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0164001 A1 | 6/2009 | Biggs et al. |
| 2009/0171437 A1 | 7/2009 | Brocker et al. |
| 2009/0192587 A1 | 7/2009 | Frid |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev et al. |
| 2010/0070019 A1 | 3/2010 | Shalev |
| 2010/0082091 A1 | 4/2010 | Berez et al. |
| 2010/0161026 A1 | 6/2010 | Brocker et al. |
| 2010/0211159 A1 | 8/2010 | Schmid et al. |
| 2010/0256725 A1 | 10/2010 | Rasmussen |
| 2010/0274187 A1 | 10/2010 | Argentine |
| 2010/0274345 A1 | 10/2010 | Rust |
| 2010/0292774 A1 | 11/2010 | Shalev |
| 2010/0318171 A1 | 12/2010 | Porter et al. |
| 2011/0022149 A1 | 1/2011 | Cox et al. |
| 2011/0022153 A1 | 1/2011 | Schreck et al. |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0218609 A1 | 9/2011 | Chobotov et al. |
| 2011/0257720 A1 | 10/2011 | Peterson et al. |
| 2011/0257725 A1 | 10/2011 | Argentine et al. |
| 2011/0262684 A1 | 10/2011 | Wintsch et al. |
| 2011/0264184 A1 | 10/2011 | Heltai |
| 2011/0288622 A1 | 11/2011 | Chan et al. |
| 2011/0301702 A1 | 12/2011 | Rust et al. |
| 2011/0319983 A1 | 12/2011 | Zhu et al. |
| 2012/0143317 A1 | 6/2012 | Cam et al. |
| 2012/0150274 A1 | 6/2012 | Shalev et al. |
| 2012/0158038 A1 | 6/2012 | Leschinsky |
| 2012/0172929 A1 | 7/2012 | Shalev |
| 2012/0179236 A1 | 7/2012 | Benary et al. |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |
| 2012/0330399 A1 | 12/2012 | Shalev et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0131783 A1 | 5/2013 | Shalev et al. |
| 2013/0204343 A1 | 8/2013 | Shalev |
| 2013/0261994 A1 | 10/2013 | Raz et al. |
| 2013/0274866 A1 | 10/2013 | Cox et al. |
| 2013/0289587 A1 | 10/2013 | Shalev |
| 2013/0297005 A1 | 11/2013 | Shalev |
| 2014/0052236 A1 | 2/2014 | Shalev |
| 2014/0172072 A1 | 6/2014 | Shalev |
| 2014/0288635 A1 | 9/2014 | Shalev |
| 2014/0324154 A1 | 10/2014 | Shalev |
| 2014/0364930 A1 | 12/2014 | Strauss et al. |

FOREIGN PATENT DOCUMENTS

| | | |
|---|---|---|
| CN | 2817770 | 9/2006 |
| CN | 201058061 | 5/2008 |
| EP | 1177780 | 2/2002 |
| EP | 1325716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| JP | 2002253682 | 9/2002 |
| WO | 99/13808 | 3/1999 |
| WO | 9934748 | 7/1999 |
| WO | WO02083038 | 10/2002 |
| WO | WO03099108 | 12/2003 |
| WO | WO2004017868 | 3/2004 |
| WO | WO2005002466 | 1/2005 |
| WO | 2005/034809 | 4/2005 |
| WO | WO2005037138 | 4/2005 |
| WO | WO2005041781 | 5/2005 |
| WO | WO2005041783 | 5/2005 |
| WO | WO2005046524 | 5/2005 |
| WO | WO2006007389 | 1/2006 |
| WO | WO2006028925 | 3/2006 |
| WO | WO2006070372 | 7/2006 |
| WO | WO2007022495 | 2/2007 |
| WO | WO2007039587 | 4/2007 |
| WO | WO2007084547 | 7/2007 |
| WO | WO2007144782 | 12/2007 |
| WO | WO2008008291 | 1/2008 |
| WO | WO2008035337 | 3/2008 |
| WO | WO2008042266 | 4/2008 |
| WO | WO2008047092 | 4/2008 |
| WO | WO2008047354 | 4/2008 |
| WO | WO2008053469 | 5/2008 |
| WO | WO2008066923 | 6/2008 |
| WO | 2008/107885 | 9/2008 |
| WO | WO2008107885 | 9/2008 |
| WO | WO2008140796 | 11/2008 |
| WO | WO2009078010 | 6/2009 |
| WO | WO2009116041 | 9/2009 |
| WO | WO2009116042 | 9/2009 |
| WO | WO2009118733 | 10/2009 |
| WO | 2010/027704 | 3/2010 |
| WO | WO2010024869 | 3/2010 |
| WO | WO2010024879 | 3/2010 |
| WO | WO2010031060 | 3/2010 |
| WO | WO2010045238 | 4/2010 |
| WO | WO2010062355 | 6/2010 |
| WO | WO2010088776 | 8/2010 |
| WO | WO2010128162 | 11/2010 |
| WO | WO2010150208 | 12/2010 |
| WO | WO2011004374 | 1/2011 |
| WO | WO2011007354 | 1/2011 |
| WO | WO2011055364 | 5/2011 |
| WO | WO2011064782 | 6/2011 |
| WO | WO2011067764 | 6/2011 |
| WO | WO2011070576 | 6/2011 |
| WO | WO2011080738 | 7/2011 |
| WO | WO2011095979 | 8/2011 |
| WO | WO2011106532 | 9/2011 |
| WO | WO2011106533 | 9/2011 |
| WO | WO2011106544 | 9/2011 |
| WO | WO2012049679 | 4/2012 |
| WO | WO2012104842 | 8/2012 |
| WO | WO2012111006 | 8/2012 |
| WO | WO2012117395 | 9/2012 |
| WO | WO2012176187 | 12/2012 |
| WO | WO2013005207 | 1/2013 |
| WO | WO2013030818 | 3/2013 |
| WO | WO2013030819 | 3/2013 |
| WO | WO2013065040 | 5/2013 |
| WO | WO2013084235 | 6/2013 |
| WO | WO2013171730 | 11/2013 |
| WO | WO2014020609 | 2/2014 |
| WO | WO2014108895 | 7/2014 |

(56) References Cited

FOREIGN PATENT DOCUMENTS

WO    WO2014141232    9/2014
WO    WO2014188412    11/2014

OTHER PUBLICATIONS

European Search Report dated Oct. 27, 2015 which issued during the prosecution of Applicant's European App No. 10835608.0.
An English translation of an Office Action dated Jul. 2, 2014 which issued during the prosecution of Chinese Patent Application No. 201080062714.5 (relevant part).
Invitation to Pay Additional Fees dated Aug. 27, 2014, which issued during the prosecution of Applicant's PCT/IL2014/050434.
An Office Action dated Nov. 26, 2014, which issued during the prosecution of U.S. Appl. No. 13/383,128.
An Office Action dated Dec. 9, 2015, which issued during the prosecution of U.S. Appl. No. 14/416,236.
Communication dated Feb. 1, 2016 from the U.S. Patent and Trademark Office in counterpart U.S. Appl. No. 14/241,793.
Communication dated Mar. 7, 2016 from the U.S. Patent and Trademark Office in counterpart U.S. Appl. No. 14/240,600.
A non-final Office Action issued on Feb. 28, 2014 in U.S. Appl. No. 13/512,778.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
An English translation of an Office Action dated Oct. 8, 2014, which issued during the prosecution of Chinese Patent Application No. 201080036970.7.
An English translation of an Office Action dated Nov. 28, 2013, which issued during the prosecution of Chinese Patent Application No. 200880126889.0.
An English translation of an Office Action dated Jan. 28, 2014, which issued during the prosecution of Chinese Patent Application No. 201080036970.7.
An English translation of an Office Action dated May 16, 2014, which issued during the prosecution of Chinese Patent Application No. 200880126889.0.
An English translation of an Office Action dated Aug. 25, 2011, which issued during the prosecution of Chinese Patent Application No. 200880014919.9.
An English translation of an Office Action dated Feb. 16, 2013, which issued during the prosecution of Chinese Patent Application No. 200880126889.0.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
A Notice of Allowance dated Aug. 2, 2012, which issued during the prosecution of U.S. Appl. No. 12/529,936.
An Advisory Action dated Feb. 13, 2014, which issued during the prosecution of Applicant's U.S. Appl. No. 13/807,880.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 on Oct. 10, 2014.
A Restriction Requirement dated Jan. 29, 2014, which issued during the prosecution of U.S. Appl. No. 13/519,971.
An International Preliminary Report on Patentability dated Jun. 12, 2012, which issued during the prosecution of Applicant's PCT/IL2010/001037.
An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
An International Search Report and a Written Opinion both dated Apr. 18, 2011, which issued during the prosecution of Applicant's PCT/IL2010/001037.
An International Search Report and a Written Opinion both dated Aug. 4, 2011, which issued during the prosecution of Applicant's PCT/IL2010/000999.
An International Search Report and a Written Opinion both dated Aug. 31, 2012, which issued during the prosecution of Applicant's PCT/IL2012/000148.
An International Search Report and a Written Opinion both dated Dec. 3, 2010, which issued during the prosecution of Applicant's PCT/IL2010/000564.
An International Search Report and a Written Opinion both dated Feb. 4, 2011, which issued during the prosecution of Applicant's PCT/IB2010/052861.
An International Search Report and a Written Opinion both dated Jul. 13, 2012, which issued during the prosecution of Applicant's PCT/IL2012/000083.
An International Search Report and a Written Opinion both dated Jul. 17, 2012, which issued during the prosecution of Applicant's PCT/IL2012/000095.
An International Search Report and a Written Opinion both dated Jun. 14, 2013, which issued during the prosecution of Applicant's PCT/IL2012/050506.
An International Search Report and a Written Opinion both dated Jun. 28, 2011, which issued during the prosecution of Applicant's PCT/IL2011/000135.
An International Search Report and a Written Opinion both dated Jun. 30, 2009, which issued during the prosecution of Applicant's PCT/IL2008/001621.
An International Search Report and a Written Opinion both dated Mar. 10, 2011, which issued during the prosecution of Applicant's PCT/IL2010/000917.
An International Search Report and a Written Opinion both dated Mar. 11, 2009, which issued during the prosecution of Applicant's PCT/IL2007/001312.
An International Search Report and a Written Opinion both dated Mar. 15, 2013, which issued during the prosecution of Applicant's PCT/IL2012/050424.
An International Preliminary Report on Patentability dated Sep. 3, 2013, which issued during the prosecution of Applicant's PCT/IL2012/000095.
An International Search Report and a Written Opinion both dated Mar. 30, 2011, which issued during the prosecution of Applicant's PCT/IL2010/001018.
An International Search Report and a Written Opinion both dated May 23, 2011, which issued during the prosecution of Applicant's PCT/IL2010/001087.

(56) References Cited

OTHER PUBLICATIONS

An International Search Report and a Written Opinion both dated Nov. 5, 2010, which issued during the prosecution of Applicant's PCT/IL2010/000549.

An International Search Report and a Written Opinion both dated Nov. 27, 2012, which issued during the prosecution of Applicant's PCT/IL2012/000300.

An International Search Report and a Written Opinion both dated Oct. 1, 2012, which issued during the prosecution of Applicant's PCT/IL2012/000241.

An International Search Report and a Written Opinion both dated Oct. 4, 2012, which issued during the prosecution of Applicant's PCT/IL2012/000269.

An International Search Report and a Written Opinion both dated Sep. 6, 2012, which issued during the prosecution of Applicant's PCT/IL2012/000190.

An International Search Report and a Written Opinion both dated Apr. 28, 2014, which issued during the prosecution of Applicant's PCT/IL2014/050019.

An International Search Report dated Jul. 30, 2014, which issued during the prosecution of Applicant's PCT/IL2014/050174.

An International Search Report and a Written Opinion both dated Sep. 24, 2012, which issued during the prosecution of Applicant's PCT/IL2012/000060.

An International Search Report and a Written Opinion both dated Sep. 29, 2008, which issued during the prosecution of Applicant's PCT/IL2008/000287.

An International Search Report dated Nov. 26, 2013, which issued during the prosecution of Applicant's PCT/IL2013/050656.

Notice of allowance dated Jun. 24, 2014, which issued during the prosecution of Applicant's U.S. Appl. No. 13/380,278.

An International Search Report dated Nov. 28, 2014, which issued during the prosecution of Applicant's PCT/IL2014/050434.

An Interview Summary dated Feb. 28, 2012, which issued during the prosecution of U.S. Appl. No. 12/529,936.

An Office Action dated Apr. 10, 2014, which issued during the prosecution of Applicant's U.S. Appl. No. 13/807,906.

An Office Action dated Apr. 24, 2014, which issued during the prosecution of Applicant's U.S. Appl. No. 13/380,278.

An Office Action dated Dec. 2, 2013, which issued during the prosecution of U.S. Appl. No. 13/807,880.

An office Action dated Feb. 25, 2013, which issued during the prosecution of U.S. Appl. No. 13/031,871.

An Office Action dated Feb. 27, 2013, which issued during the prosecution of U.S. Appl. No. 12/808,037.

An Office Action dated Jul. 24, 2014, which issued during the prosecution of Canadian Patent Application No. 2768228.

An Office Action dated Jul. 28, 2014, which issued during the prosecution of U.S. Appl. No. 13/031,871.

An Office Action dated Jun. 19, 2012, which issued during the prosecution of U.S. Appl. No. 12/808,037.

An Office Action dated Mar. 24, 2011, which issued during the prosecution of U.S. Appl. No. 12/529,936.

An Office Action dated Mar. 28, 2014, which issued during the prosecution of Applicant's U.S. Appl. No. 13/519,971.

An Office Action dated Apr. 27, 2011, which issued during the prosecution of U.S. Appl. No. 12/447,684.

An Office Action dated Apr. 28, 2014, which issued during the prosecution of Applicant's U.S. Appl. No. 13/939,798.

An Office Action dated May 20, 2013, which issued during the prosecution of U.S. Appl. No. 13/807,880.

An Office Action dated Nov. 12, 2010, which issued during the prosecution of U.S. Appl. No. 12/447,684.

An Office Action dated Nov. 3, 2014, which issued during the prosecution of Canadian Patent Application No. 2767596.

An Office Action dated Nov. 19, 2013, which issued during the prosecution of U.S. Appl. No. 13/663,117.

An Office Action dated Oct. 11, 2012, which issued during the prosecution of U.S. Appl. No. 13/031,871.

U.S. Appl. No. 61/219,758, filed Jun. 23, 2009.

U.S. Appl. No. 61/221,074, filed Jun. 28, 2009.

U.S. Appl. No. 61/496,613, filed Jun. 14, 2011.

An Office Action dated Oct. 28, 2011, which issued during the prosecution of U.S. Appl. No. 12/529,936.

U.S. Appl. No. 61/505,132, filed Jul. 7, 2011.

U.S. Appl. No. 61/678,182, filed Aug. 1, 2012.

U.S. Appl. No. 61/529,931, filed Sep. 1, 2011.

U.S. Appl. No. 61/553,209, filed Oct. 30, 2011.

U.S. Appl. No. 61/499,195, filed Jun. 21, 2011.

U.S. Appl. No. 61/749,965, filed Jan. 8, 2013.

Notice of Allowance dated Jun. 18, 2013, which issued during the prosecution of U.S. Appl. No. 13/523,296.

Office Action issued on Oct. 27, 2014 in Canadian Patent Application No. 2,785,953.

Ryhanen J., in "Biocompatibility evaluation of nickel—titanium shape memory metal alloy," Academic Dissertation, Faculty of Medicine, Department of Surgery, University of Oulu, Finland (May 1999).

Supplementary European Search Report dated Dec. 13, 2012, which issued during the prosecution of Applicant's European App No. 08719912.1.

Supplementary European Search Report dated Feb. 17, 2014, which issued during the prosecution of Applicant's European App No. 12803376.8.

Supplementary European Search Report dated Jun. 23, 2014, which issued during the prosecution of Applicant's European App No. 12741804.4.

Written Opinion dated Nov. 26, 2013, which issued during the prosecution of Applicant's PCT/IL2013/050656.

"E-vita® open plus" product brochure (JOTEC GmbH, Hechingen, Germany), 2010.

An Office action dated Sep. 4, 2014, from the U.S. Patent and Trademark Office in counterpart U.S. Appl. No. 13/519,971.

European Office Action issued Dec. 17, 2014 in European Patent Application No. 12803376.8.

An Office action dated Feb. 5, 2015, from the U.S. Patent and Trademark Office in counterpart U.S. Appl. No. 13/384,075.

European Search Report issued Feb. 24, 2014 in European Patent Application No. 12803376.8.

Fattori et al., Degenerative aneurysm of the descending aorta. Endovascular Treatment. pp. 1-11, 2007, European Association for Cardio-Thoracic Surgery.

International Preliminary Report on Patentability dated Jan. 12, 2010 in corresponding International Application No. PCT/IL2008/000287.

Fonseca A et al., "Intravascular ultrasound assessment of the novel AngioSculpt scoring balloon catheter for the treatment of complex coronary lesions," J Invasive Cardiol 20(1):21-7 (Jan. 2008).

Van Prehn J et al., "Oversizing of aortic stent grafts for abdominal aneurysm repair: a systematic review of the benefits and risks," Eur J Vasc Endovase Surg. Jul. 2009;38(I):42-53. Epub May 9, 2009 (abstract only).

Invitation to Pay Additional Fees dated May 13, 2014, which issued during the prosecution of Applicant's PCT/IL2014/050019.

Invitation to Pay Additional Fees dated May 8, 2014, which issued during the prosecution of Applicant's PCT/IL2014/50174.

Khlif H et al., "Contribution to the Improvement of Textile Vascular Prostheses Crimping," Trends in Applied Sciences Research 6(9):1019-1027 (2011).

U.S. Appl. No. 61/775,964, filed Mar. 11, 2013.

U.S. Appl. No. 61/826,544, filed May 23, 2013.

U.S. Appl. No. 61/906,014, filed Nov. 19, 2013.

U.S. Appl. No. 61/926,533, filed Jan. 13, 2014.

U.S. Appl. No. 61/528,242, filed Aug. 28, 2011.

An Office Action dated Aug. 15, 2014, which issued during the prosecution of Applicant's U.S. Appl. No. 13/939,798.

An English translation of an Office Action dated Mar. 19, 2015, which issued during the prosecution of Chinese Patent Application No. 201080036970.7.

A Notice of Allowance dated Jan. 20, 2015, which issued during the prosecution of U.S. Appl. No. 13/383,128.

A Notice of Allowance dated Nov. 7, 2014, which issued during the prosecution of U.S. Appl. No. 13/512,778.

(56) References Cited

OTHER PUBLICATIONS

An Office Action dated Aug. 15, 2014, which issued during the prosecution of U.S. Appl. No. 13/512,778.
An International Search Report and a Written Opinion both dated Mar. 18, 2015, which issued during the prosecution of Applicant's PCT/IL2014/050973.
An Office Action dated Apr. 14, 2015, which issued during the prosecution of U.S. Appl. No. 14/130,213.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.
An Office Action dated Mar. 26, 2015, which issued during the prosecution of U.S. Appl. No. 13/514,240.
Supplementary European Search Report dated Oct. 31, 2014, which issued during the prosecution of Applicant's European App No. 12752054.2.
An Office Action dated Sep. 2, 2014, which issued during the prosecution of U.S. Appl. No. 12/447,684.
U.S. Appl. No. 61/448,199, filed Mar. 2, 2011.
U.S. Appl. No. 61/014,031, filed Dec. 15, 2007.
An Examiner Interview Summary dated Dec. 13, 2010, which issued during the prosecution of U.S. Appl. No. 12/447,684.
An Office Action dated Mar. 21, 2012, which issued during the prosecution of U.S. Appl. No. 12/808,037.
An Office Action dated May 22, 2013, which issued during the prosecution of U.S. Appl. No. 12/808,037.
U.S. Appl. No. 60/863,373, filed Oct. 29, 2006.
An International Preliminary Report on Patentability dated Aug. 21, 2013, which issued during the prosecution of Applicant's PCT/IL2012/000083.

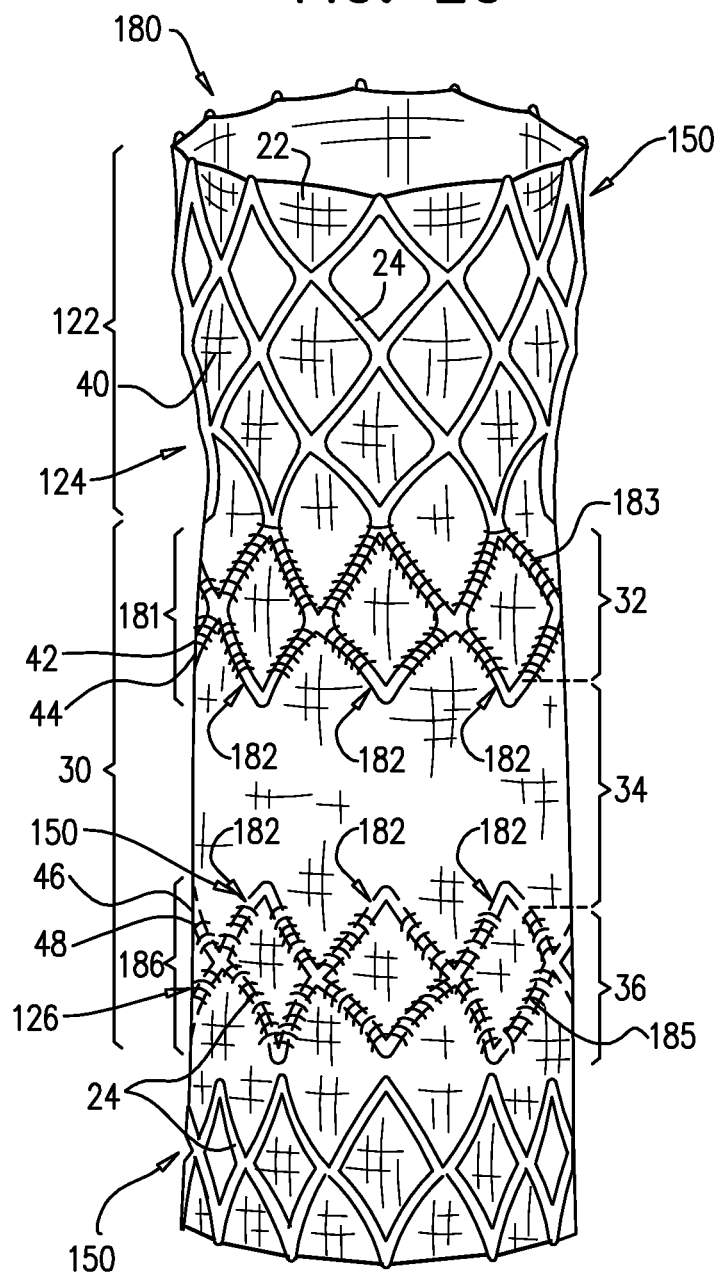

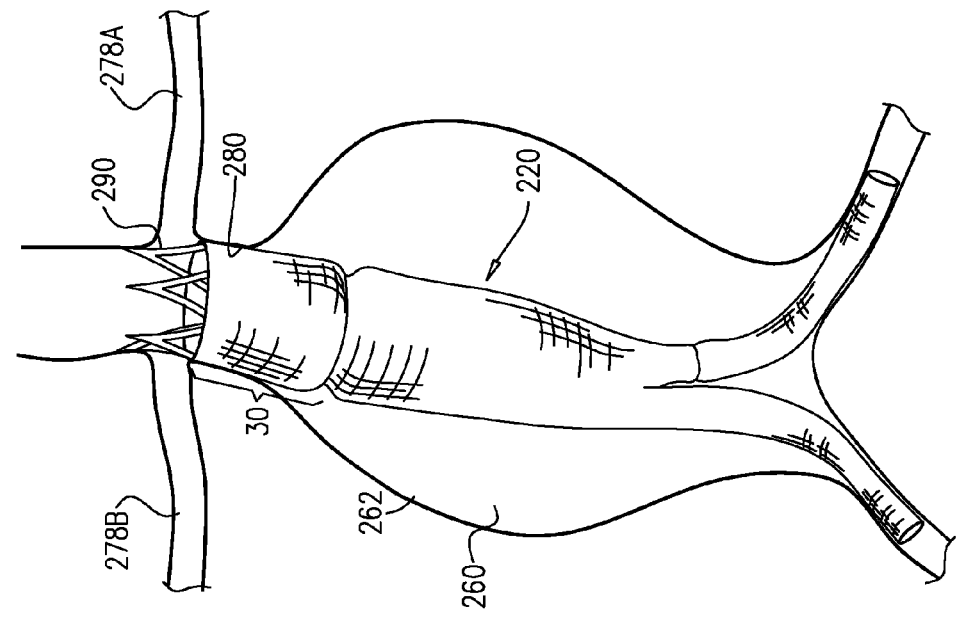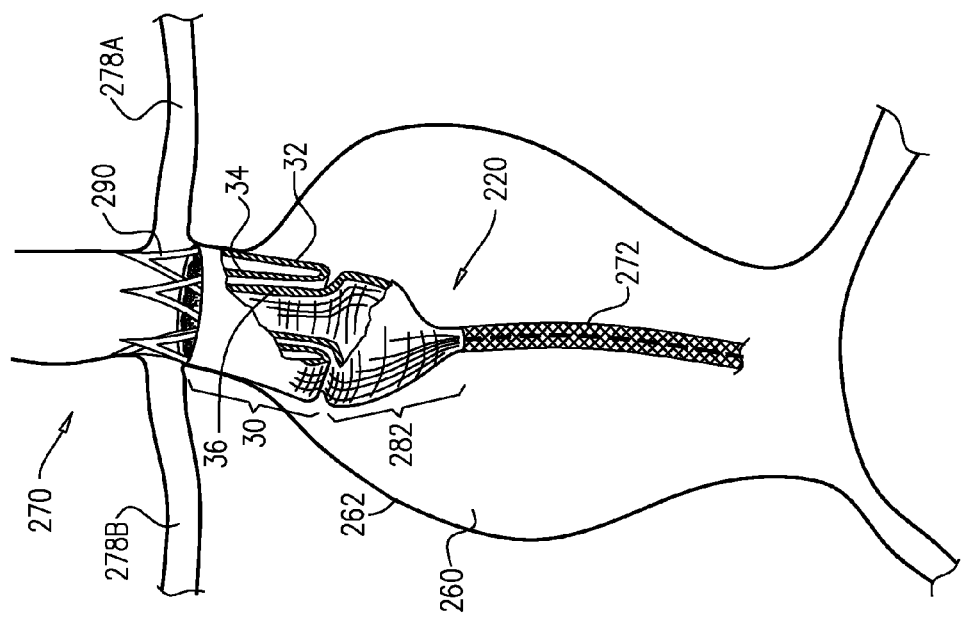

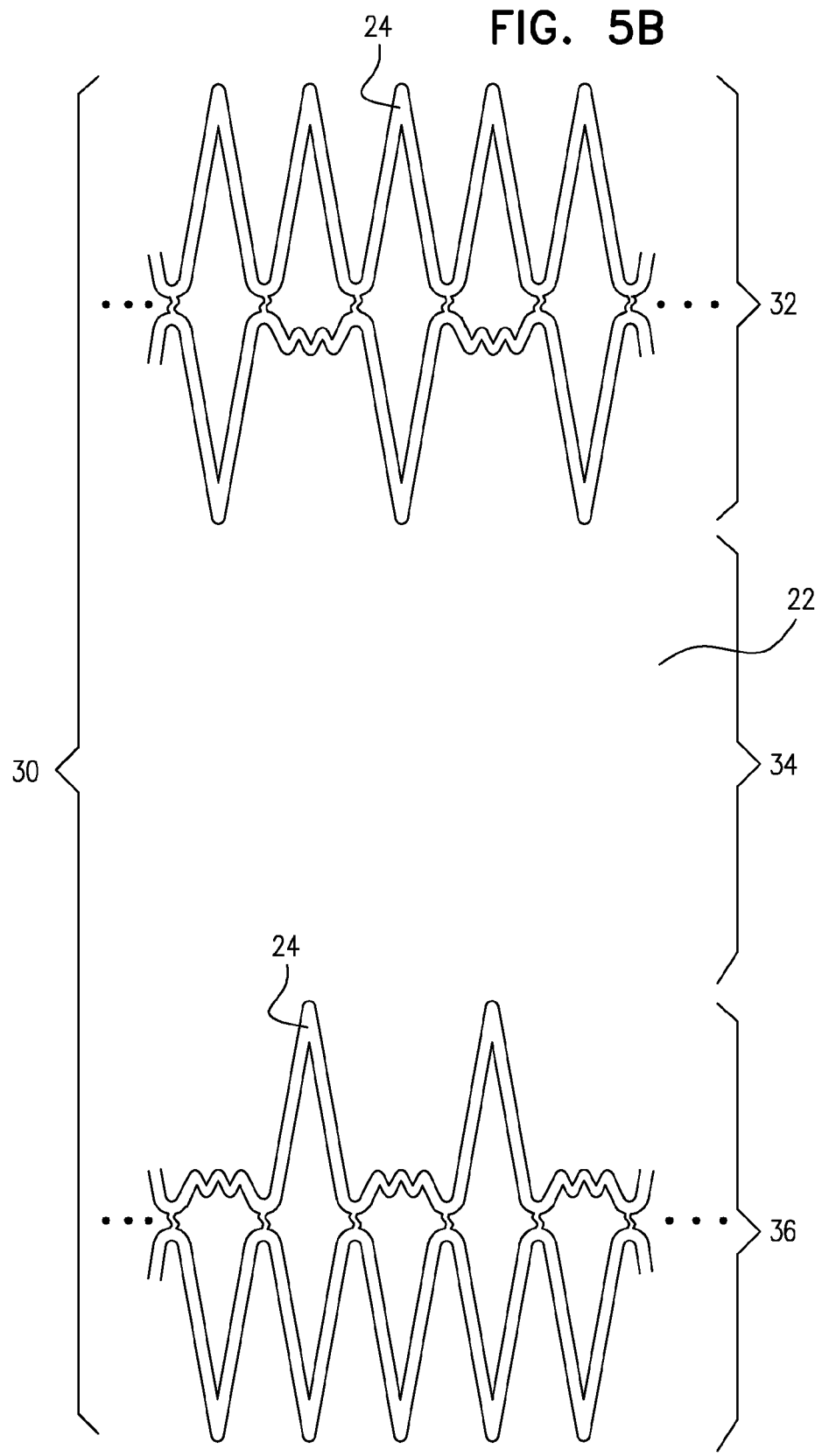

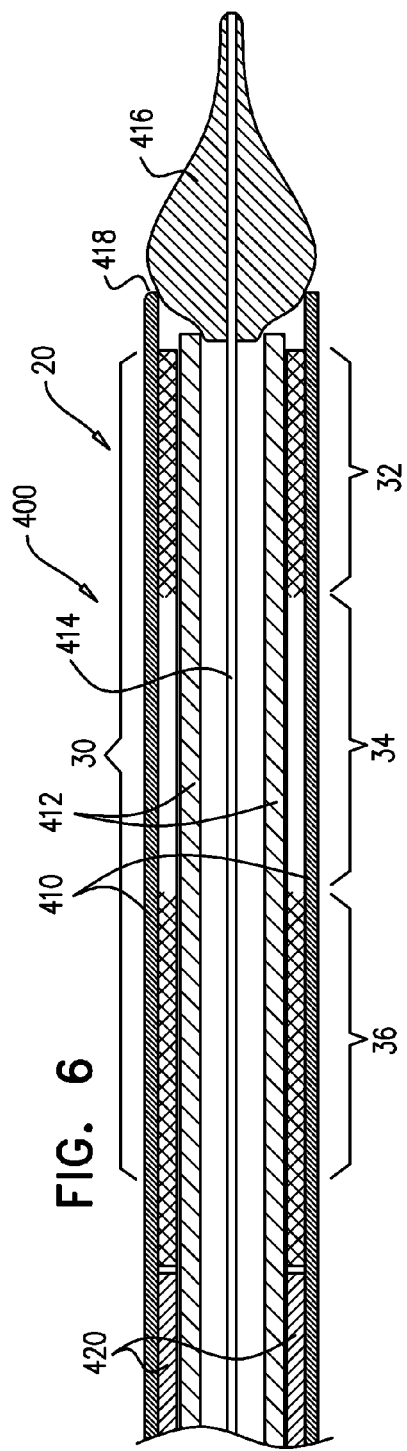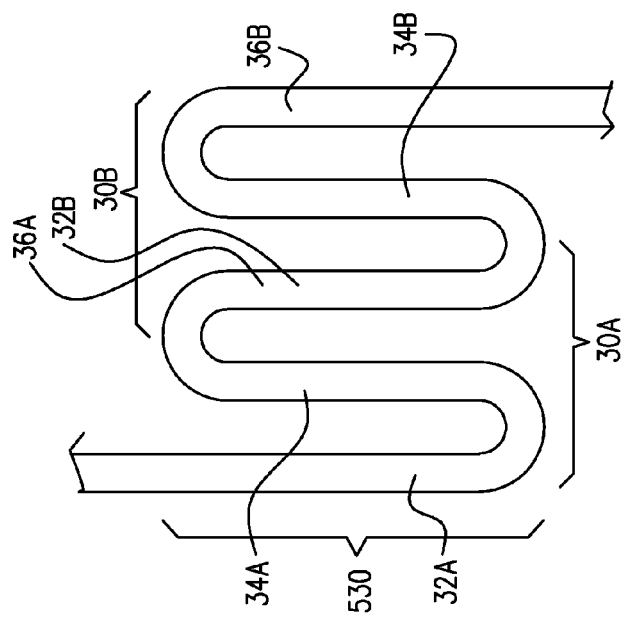
FIG. 6
FIG. 7

TRIPLE-COLLAR STENT-GRAFT

CROSS-REFERENCE TO RELATED APPLICATIONS

The present application is the U.S. national stage of International Application PCT/IL2012/050424, filed Oct. 29, 2012, which claims priority from U.S. Provisional Application 61/553,209, filed Oct. 30, 2011, which is assigned to the assignee of the present application and is incorporated herein by reference.

FIELD OF THE APPLICATION

This present application relates generally to prostheses and surgical methods, and specifically to tubular prostheses, including endovascular stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms which commonly form between the renal arteries and the iliac arteries are referred to as abdominal aortic aneurysms ("AAAs"). Other aneurysms occur in the aorta, such as thoracic aortic aneurysms ("TAAs"), which may occur in one or more of the descending aorta, the ascending aorta, and the aortic arch.

Endo-Vascular Aneurysm Repair (EVAR) has transformed the practice of treatment of aortic aneurysms from an open surgical approach to a much less invasive surgical approach. The first step of an endovascular intervention usually requires introducing a delivery system into the vasculature of a subject. If the crossing profile, i.e., the external diameter, of the delivery system is 14 Fr or lower (3 Fr=1 millimeter), a true percutaneous approach may be used, because vascular closure devices are available for proper closure of such puncture sites. If the crossing profile at least 15-16 Fr, a vascular cut-down is usually required in advance as a preparatory step to introduction of the delivery system.

Endovascular systems for treatment of supra-renal aneurysms generally require the preparatory step of a vascular cut-down. A cut-down is the localized surgical exposure of blood vessels for accessing the subject's vasculature. For example, most surgical cut-downs used in EVAR procedures are performed in the vicinity of the pubis, exposing the iliac arteries. Surgical cut-downs have related complications and co-morbidities, including difficulty in controlling bleeding at the access site, false aneurysms, and vascular obstruction. It is therefore desirable to use a purely percutaneous approach, instead of a vascular cut-down.

Endovascular stent-grafts for treating the thoracic aorta usually require a 20-22 Fr delivery system, because of the large amount of graft material indicated by the diameter of the aorta above the level of the renal arteries (30-40 mm diameter or more in some subjects). Currently used graft materials are PET (Poly Ethylene Therephtalate) and ePTFE (expanded Poly-Tetra-Fluoro-Ethylene). The thickness and circumferential length of the graft have the most substantial effect on the crossing profile of an endovascular system. The use of thinner graft materials generally reduces long-term durability of the graft material.

"Endoleak" is the persistent flow of blood into the aneurismal sac after implantation of an endovascular prosthesis. The management of some types of endoleak remains controversial, although most can be successfully occluded with surgery, further stent implantation, or embolization. Four types of endoleaks have been defined, based upon their proposed etiology: Type I endoleak, described below; Type II endoleak, characterized by flow into and out of the aneurismal sac from patent branch vessels; Type III endoleak, characterized by flow into the aneurismal sac from separation between components of a modular system; and Type IV endoleak, characterized by egress of blood through the pores in the fabric.

A type I endoleak, which occurs in up to 10 percent of endovascular aortic aneurysm repairs, is due to an incompetent seal at either the proximal or distal attachment sites of the vascular prosthesis, resulting in blood flow at the end of the prosthesis into the aneurismal sac. Etiologies include undersizing of the diameter of the endograft at the attachment site and ineffective attachment to a vessel wall that is heavily calcified or surrounded by thick thrombus. Type I failures have also been found to be caused by a continual expansion of the aneurysm neck (the portion of the aorta extending cephalad or caudad from the aneurysm, and is not dilated). This expansion rate has been estimated to be about one millimeter per year. Because the aneurysm neck expands beyond the natural resting diameter of the prosthesis, one or more passageways are defined about the prosthesis in communication with the aneurismal sac. Additionally, Type I endoleaks may be caused when circular prostheses are implanted in non-circular aortic lumens, which may be caused by irregular vessel formation and/or calcified topography of the lumen of the aorta.

Type I endoleaks may occur immediately after placement of the prosthesis, or may be delayed. A delayed type I endoleak may be seen during follow-up studies if the prosthesis is deployed into a diseased segment of aorta that dilates over time, leading to a breach in the seal at the attachment site.

Type I endoleaks must be repaired as soon as they are discovered, because the aneurismal sac remains exposed to systemic pressure, predisposing to aneurysmal rupture, and spontaneous closure of the leak is rare. If discovered at the time of initial placement, repair may consist of reversal of anticoagulation and reinflation of the deployment balloon for an extended period of time. These leaks may also be repaired with small extension grafts that are placed over the affected end. These methods are usually sufficient to exclude the aneurysm. Conversion to an open surgical repair may be needed in the rare situation in which the leak is refractory to percutaneous treatment.

As can be readily appreciated, even with the successful implantation of an endovascular prosthesis, failures may occur thereafter. It has been found that type I endoleak failures may affect up to 5-10% of all implanted prostheses. Accordingly, there is a clear need for an endovascular prosthesis which can reduce the likelihood of, and ideally eliminate, type I endoleak failures.

SUMMARY OF APPLICATIONS

Some applications of the present invention provide a stent-graft that is configured to define at least one generally tubular foldable section, which comprises first, second, and third subsections. The stent-graft is configured to initially assume a radially-compressed delivery configuration, in which the foldable section is in a longitudinally-expanded state, such that the first and the third subsections longitudinally surround the second subsection. During endoluminal deployment in a body lumen, such as a blood vessel, the stent-graft transitions to a radially-expanded deployment configuration, in which the foldable section is longitudinally folded. In this folded state, the second subsection is radially sandwiched between the first and the third subsections. As a result, the second subsection at least partially longitudinally overlaps with both the first and the third subsections, thereby thickening the graft material of the stent-graft.

This thickening of the stent-graft may provide improved sealing between the stent-graft and a blood vessel wall, such as at the neck of an aneurysm. Such improved sealing may reduce the risk of type I endoleak, and/or provide improved structural support, without increasing the crossing profile of the stent-graft during transvascular introduction in the longitudinally-expanded delivery configuration. Graft material generally has the most significant effect on the crossing profile of a stent-graft. The stent-graft achieves a low crossing profile during transvascular introduction in a catheter, because the graft material of the stent-graft is longitudinally stretched in the delivery configuration. The stent-graft thus can typically be deployed using a catheter having a diameter of no more than 28 Fr, such as no more than 22 Fr, e.g., no more than 14 Fr. These diameters, particularly as they approach 14 Fr, generally enable the use of a true percutaneous surgical technique, without the need for a vascular cut-down.

For some applications, during a first stage of an implantation procedure, the stent-graft is transvascularly (typically percutaneously) introduced into a blood vessel, such as an aorta, while positioned in a delivery catheter. The delivery catheter is advanced to a desired deployment location in the blood vessel, such at or slightly above the renal arteries. The delivery catheter is proximally withdrawn, releasing the first subsection of the foldable section in the aorta. The first subsection radially expands as it is released, until it comes in contact with a wall of the blood vessel, e.g., a sub-renal neck of an aneurysm. The delivery catheter is further proximally withdrawn, releasing the second subsection of the foldable section in the aorta. The second subsection radially expands as it is released.

In order to fold the foldable section, the surgeon distally advances the delivery catheter, thereby folding the second subsection within the first subsection. As a result, the first and the second subsections longitudinally overlap. The surgeon further proximally withdraws the delivery catheter, thereby releasing the third subsection within both the first and the second subsections. The third subsection radially expands as it is released from the catheter, thereby completing the transition of the foldable section to its longitudinally-folded state. In this folded state, the second subsection is radially sandwiched between the first and the third subsections.

For some applications, the stent-graft is a first stent-graft, which is deployed in a side-facing fenestration of a second stent-graft. During an implantation procedure, the second stent-graft is deployed in a blood vessel, and assumes a radially-expanded state. The first stent-graft, while in the deployment configuration in a delivery catheter, is passed partially through the side-facing fenestration of the second stent-graft. The delivery catheter is proximally withdrawn, releasing the first subsection, which radially expands as it is released.

The surgeon folds the foldable section of the stent-graft, by (a) proximally withdrawing the delivery catheter, thereby releasing the second subsection of the foldable section, which radially expands, (b) distally advancing the delivery catheter further through the fenestration, thereby folding the second subsection within the first subsection, such that the first and the second subsections longitudinally overlap, and (c) further proximally withdrawing the delivery catheter, thereby releasing the third subsection within both the first and the second subsections.

As a result, the foldable section assumes its longitudinally-folded state, such that the second subsection is radially sandwiched between the first and the third subsections. The foldable section of the first stent-graft is dimensioned to be fixed to the side-facing fenestration, when the second stent-graft is in a radially-expanded state and foldable section 30 is in its longitudinally-folded state. This folding of the foldable section thickens the graft material of the stent-graft, thereby providing improved sealing between the first stent-graft and the fenestration. In addition, the folding typically doubles or triples the number of structural support elements of the stent-graft along the foldable section, thereby providing improved structural support at the junction between the first and the second stent-grafts.

There is therefore provided, in accordance with an application of the present invention, apparatus including an endovascular stent-graft, which includes:

a fluid flow guide; and a plurality of structural stent elements attached to at least a portion of the fluid flow guide, wherein the stent-graft is configured (a) to define a generally tubular foldable section, which includes first, second, and third subsections, and (b) to assume:

a delivery configuration, in which (a) the stent-graft, including the foldable section, is in a radially-compressed state, and (b) the foldable section is in a longitudinally-expanded state, in which state the first and the third subsections longitudinally surround the second subsection, and a deployment configuration, in which (a) the stent-graft, including the foldable section, is in a radially-expanded state, and (b) the foldable section is in a longitudinally-folded state, such that the second subsection is radially sandwiched between the first and the third subsections.

For some applications, an average surface coverage ratio of the structural stent elements on the fluid flow guide along the second subsection is no more than 20%, such as no more than 10%, of the greater of (a) an average surface coverage ratio of the structural stent elements on the fluid flow guide along the first subsection and (b) an average surface coverage ratio of the structural stent elements on the fluid flow guide along the third subsection. For some applications, none of the structural stent elements is disposed along the second subsection. For some applications, a first subgroup of the structural stent elements is attached to the first subsection, and a second subgroup of the structural stent elements is attached to the third subsection. For some applications, one of the first and the second subgroups of the structural stent elements is attached to an internal surface of the fluid flow guide, and the other of the first and the second subgroups is attached to an external surface of the fluid flow guide. For some applications, the first subgroup is attached to the external surface, and the second subgroup is attached to the internal surface.

For some applications, an evertibility of the second subsection is greater than an evertibility of the first subsection, and is greater than an evertibility of the third subsection.

For some applications, a first subgroup of the structural stent elements is attached to the first subsection, and a second subgroup of the structural stent elements is attached to the third subsection; and one of the first and the second subgroups of the structural stent elements is attached to an internal surface of the fluid flow guide, and the other of the first and the second subgroups is attached to an external surface of the fluid flow guide. For some applications, the first subgroup is attached to the external surface, and the second subgroup is attached to the internal surface.

For some applications, when the stent-graft is in the delivery configuration, the first and the second subsections are arranged longitudinally contiguously, and the second and the third subsections are arranged longitudinally contiguously.

For some applications, a first subgroup of the structural stent elements are attached to the fluid flow guide along the first subsection, and at least partially curves inwardly, when the foldable section is in the longitudinally-folded state. For some applications, the first subsection has first and second longitudinal edges, which second edge joins a third longitudinal edge of the second subsection; the stent-graft is configured to define, in addition to the foldable section, a generally tubular proximal portion that extends from the first longitudinal edge of the first subsection in a direction away from the second subsection; and a second subgroup of the structural stent elements are disposed along the proximal portion, and do not curve inwardly. For some applications, the first subsection has first and second longitudinal edges, which second edge joins a third longitudinal edge of the second subsection, and an at least partially inwardly-curved portion of the first subgroup extends to a border between the second and the third longitudinal edges. For some applications, none of the structural stent elements is disposed along the second subsection.

For some applications, a second subgroup of the structural stent elements are attached to the fluid flow guide along the third subsection, and at least partially curves inwardly, when the foldable section is in the longitudinally-folded state.

For some applications, first and second subgroups of the structural stent elements are attached to the fluid flow guide along the first and the third subsections, respectively, and the first and the second subgroups are shaped to interlock the first and the third subsections when the foldable section is in the longitudinally-folded state.

For some applications, the structural stent elements are arranged as a plurality of generally circumferential bands.

For some such applications, one of the circumferential bands includes first portions and second portions; when the foldable section is in its longitudinally-expanded state, the first portions are disposed along at least a portion of the first subsection, and the second portions are disposed along a portion of the second subsection; and the first portions are at least partially attached to the fluid flow guide along the first subsection, and the second portions are not attached to the fluid flow guide. For some applications, one of the circumferential bands includes first portions and second portions; when the foldable section is in its longitudinally-expanded state, the first portions are disposed along at least a portion of the third subsection, and the second portions are disposed along a portion of the second subsection; and the first portions are at least partially attached to the fluid flow guide along the third subsection, and the second portions are not attached to the fluid flow guide.

For some such applications, one of the circumferential bands is attached to the fluid flow guide along the first subsection, and at least partially curves inwardly, when the foldable section is in the longitudinally-folded state.

For some such applications, one of the circumferential bands is attached to the fluid flow guide along the third subsection, and at least partially curves inwardly, when the foldable section is in the longitudinally-folded state.

For some such applications, first and second ones of the circumferential bands are attached to the fluid flow guide along the first and the third subsections, respectively, and the first and the second circumferential bands are shaped to interlock the first and the third subsections when the foldable section is in the longitudinally-folded state.

For some such applications, the first subsection has first and second longitudinal edges, which second edge joins a third longitudinal edge of the second subsection, and one of the circumferential bands is attached to the fluid flow guide along the first subsection, and longitudinally protrudes beyond the first longitudinal edge of the first subsection.

For some applications, the stent-graft is a first stent-graft; the apparatus further includes a second stent-graft, which is shaped so as to define a side-facing fenestration; and the foldable section of the first stent-graft is dimensioned to be fixed to the side-facing fenestration, when the second stent-graft is in a radially-expanded state and the foldable section is in the longitudinally-folded state.

For some applications, the foldable section includes first and second foldable sections; and the third subsection of the first foldable section serves also as the first subsection of the second foldable section, such that the first foldable section partially longitudinally overlaps the second foldable section when the stent-graft is in the deployment configuration.

For some applications, the stent-graft is self-expandable.

For some applications, the structural stent elements include a superelastic alloy, such as Nitinol. For some applications, the structural stent elements include a shape memory alloy.

For some applications, the fluid flow guide includes a polyester, or a polyethylene, such as a poly-ethylene-terephthalate.

For some applications, the stent-graft further includes a plurality of circumferentially-disposed radiopaque markers. For some applications:
  the first subsection has first and second longitudinal edges,
  the second subsection has third and fourth longitudinal edges,
  the third subsection has fifth and sixth longitudinal edges,
  the second edge joins the third edge,
  the fourth edge joins the fifth edge, and
  a first subset of the radiopaque markers are disposed near the first edge of the first subsection, and a second subset of the radiopaque markers are disposed near the fifth edge of the third subsection.

For some applications, the radiopaque markers are disposed in angularly overlapping arrays.

For some applications, the apparatus further includes an elongated delivery tool, which includes a tubular external shaft and an internal shaft, which is slidably disposed within the external shaft, and the stent-graft is initially disposed, in the delivery configuration, between the external and the internal shafts of the delivery tool, in a vicinity of a distal end of the external shaft. For some applications, the delivery tool further includes a stopper member fixed to the internal shaft, which is initially disposed proximally adjacent the stent-graft, thereby preventing proximal movement of the stent-graft inside the delivery tool when the external shaft is withdrawn proximally relative to the internal shaft.

There is further provided, in accordance with an application of the present invention, a method including:

providing an endovascular stent-graft, which includes a fluid flow guide, and a plurality of structural stent elements attached to at least a portion of the fluid flow guide, wherein the stent-graft is configured to define a generally tubular foldable section, which includes first, second, and third subsections;

transvascularly introducing the stent-graft into a blood vessel of a human subject while the stent-graft is in a delivery configuration, in which (a) the stent-graft, including the foldable section, is in a radially-compressed state, and (b) the foldable section is in a longitudinally-expanded state, in which state the first and the third subsections longitudinally surround the second subsection; and thereafter, transitioning the stent-graft to a deployment configuration in the blood vessel, in which configuration (a) the stent-graft, including the foldable section, is in a radially-expanded state, and (b) the foldable section is in a longitudinally-folded state, such that the second subsection is radially sandwiched between the first and the third subsections.

For some applications, providing the stent-graft includes providing the stent-graft in which an average surface coverage ratio of the structural stent elements of the structural stent elements on the fluid flow guide along the second subsection is no more than 20% of the greater of (a) an average surface coverage ratio of the structural stent elements on the fluid flow guide along the first subsection and (b) an average surface coverage ratio of the structural stent elements on the fluid flow guide along the third subsection. For some applications, providing the stent-graft includes providing the stent-graft in which none of the structural stent elements is disposed along the second subsection. For some applications, providing the stent-graft includes providing the stent-graft in which a first subgroup of the structural stent elements is attached to the first subsection, and a second subgroup of the structural stent elements is attached to the third subsection. For some applications, providing the stent-graft includes providing the stent-graft in which one of the first and the second subgroups of the structural stent elements is attached to an internal surface of the fluid flow guide, and the other of the first and the second subgroups is attached to an external surface of the fluid flow guide. For some applications, providing the stent-graft includes providing the stent-graft in which the first subgroup is attached to the external surface, and the second subgroup is attached to the internal surface.

For some applications, providing the stent-graft includes providing the stent-graft in which an evertibility of the second subsection is greater than an evertibility of the first subsection, and is greater than an evertibility of the third subsection.

For some applications, providing the stent-graft includes providing the stent-graft in which: a first subgroup of the structural stent elements is attached to the first subsection, a second subgroup of the structural stent elements is attached to the third subsection, one of the first and the second subgroups of the structural stent elements is attached to an internal surface of the fluid flow guide, and the other of the first and the second subgroups is attached to an external surface of the fluid flow guide. For some applications, providing the stent-graft includes providing the stent-graft in which the first subgroup is attached to the external surface, and the second subgroup is attached to the internal surface.

For some applications, transitioning includes transitioning the stent-graft to the deployment configuration in which the first and the second subsections are arranged longitudinally contiguously, and the second and the third subsections are arranged longitudinally contiguously.

For some applications, providing the stent-graft includes providing the stent-graft in which a first subgroup of the structural stent elements are attached to the fluid flow guide along the first subsection, and at least partially curves inwardly, when the foldable section is in the longitudinally-folded state.

For some applications, providing the stent-graft includes providing the stent-graft in which a second subgroup of the structural stent elements are attached to the fluid flow guide along the third subsection, and at least partially curves inwardly, when the foldable section is in the longitudinally-folded state.

For some applications, providing the stent-graft includes providing the stent-graft in which first and second subgroups of the structural stent elements are attached to the fluid flow guide along the first and the third subsections, respectively, and transitioning the stent-graft to the deployment configuration includes interlocking the first and the third subsections.

For some applications, the stent-graft is a first stent-graft, and the method further includes:

providing a second stent-graft, which is shaped so as to define a side-facing fenestration;

transvascularly introducing the second stent-graft into the subject; and positioning the foldable section of the first stent-graft inside the side-facing fenestration, and transitioning includes transitioning the first stent-graft to the deployment configuration while positioned in the side-facing fenestration, thereby fixing the first stent-graft to the side-facing fenestration.

For some applications, transitioning the stent-graft to the deployment configuration includes allowing the stent-graft to self-expand.

For some applications, providing the stent-graft includes providing the stent-graft in which the stent-graft further includes a plurality of circumferentially-disposed radiopaque markers. For some applications:

the first subsection has first and second longitudinal edges, the second subsection has third and fourth longitudinal edges, the third subsection has fifth and sixth longitudinal edges, the second edge joins the third edge, the fourth edge joins the fifth edge, providing the stent-graft includes providing the stent-graft in which a first subset of the radiopaque markers are disposed near the first edge of the first subsection, and a second subset of radiopaque markers are disposed near the fifth edge of the third subsection, and transitioning the stent to the deployment configuration includes ascertaining that the foldable section has fully assumed the longitudinally-folded state by observing that the first and the second subsets of the radiopaque markers are longitudinally aligned with each other.

For some applications, transvascularly introducing includes transvascular introducing the stent-graft into the blood vessel while the stent-graft is initially disposed, in the delivery configuration, between a tubular external shaft and an internal shafts of an elongated delivery tool, in a vicinity of a distal end of the external shaft. For some applications, the delivery tool further includes a stopper member fixed to the internal shaft, transvascularly introducing includes transvascularly introducing the stent-graft while the stopper member is initially disposed proximally adjacent the stent-graft, and transitioning the stent-graft to the deployment configuration includes withdrawing the external shaft proximally relative to the internal shaft, such that the stopper member prevents proximal movement of the stent-graft inside the delivery tool.

The present invention will be more fully understood from the following detailed description of applications thereof, taken together with the drawings, in which:

BRIEF DESCRIPTION OF THE DRAWINGS

FIG. 2C is a schematic illustration of an endovascular stent-graft, in accordance with an application of the present invention;

FIGS. 3A-F are schematic illustrations of an exemplary method of deploying an endovascular stent-graft in the vicinity of an sub-renal abdominal aortic aneurysm of an abdominal aorta, in accordance with an application of the present invention;

FIGS. 5A and 5B are exemplary stent patterns, in accordance with respective applications of the present invention;

FIG. 6 is a schematic cross-sectional illustration of an elongated delivery tool, in accordance with an application of the present invention; and FIG. 7 is a schematic cross-sectional illustration of one wall of a doubled foldable section of an endovascular stent-graft, in accordance with an application of the present invention.

DETAILED DESCRIPTION OF APPLICATIONS

Applications of the present invention provide a foldable endovascular stent-graft.

Figure 1:
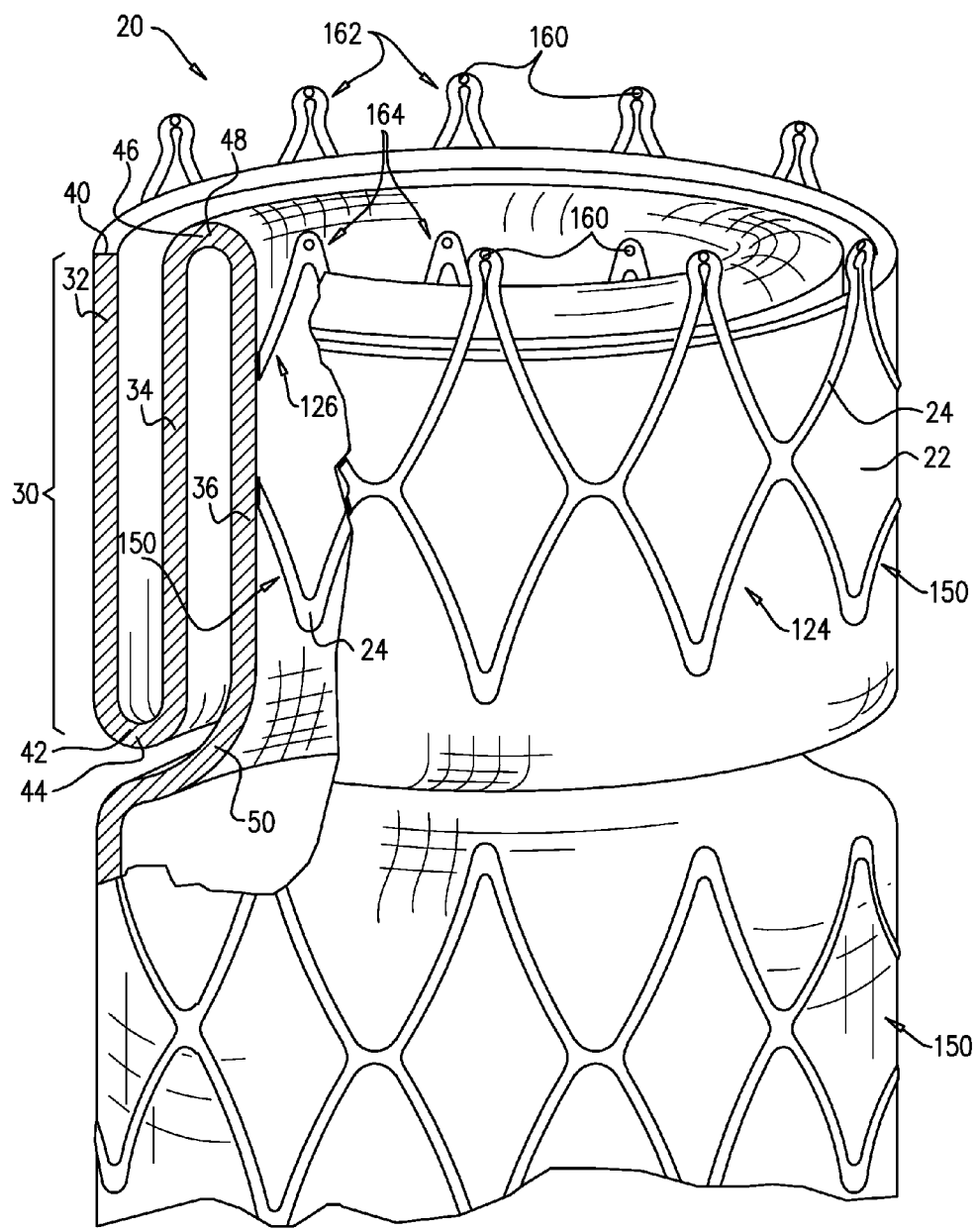
FIG. 1 is a schematic illustration of an endovascular stent-graft, in accordance with an application of the present invention.

FIG. 1 is a schematic illustration of a stent-graft 20, in accordance with an application of the present invention. Stent-graft 20 is one configuration of the foldable endovascular stent-graft provided in applications of the present invention. Endovascular stent-graft 20 is configured to initially be positioned in a delivery catheter in a delivery configuration, as described hereinbelow with reference to FIG. 3A, and to assume a deployment configuration upon being deployed from the delivery catheter, as described hereinbelow with reference to FIGS. 3B-F. FIG. 1 shows the endovascular stent-graft in the deployment configuration.

Stent-graft 20 comprises a fluid flow guide 22, and a plurality of structural stent elements 24 attached to at least a portion of the fluid flow guide, such as by suturing or stitching. Structural stent elements 24 may be attached to an internal surface and/or an external surface of the fluid flow guide. Optionally, a portion of the structural stent elements may be attached (e.g., sutured) to the internal surface, and another portion to the external surface. For some applications, structural stent elements 24 comprise a metal. Alternatively or additionally, the structural stent elements comprise a self-expanding material, such that stent-graft 20 is self-expandable. Alternatively or additionally, the structural stent elements comprise a superelastic metal alloy, a shape memory metallic alloy, and/or Nitinol. For some applications, the stent-graft is heat-set to assume the radially-expanded state.

Fluid flow guide 22 comprises at least one biologically-compatible substantially blood-impervious flexible sheet. The flexible sheet may comprise, for example, a polyester, a polyethylene (e.g., a poly-ethylene-terephthalate), a polymeric film material (e.g., polytetrafluoroethylene), a polymeric textile material (e.g., woven polyethylene terephthalate (PET)), natural tissue graft (e.g., saphenous vein or collagen), or a combination thereof.

Stent-graft 20 is configured to define at least one generally tubular foldable section 30, which comprises a first subsection 32, a second subsection 34, and a third subsection 36. For some applications, such as shown in FIGS. 1, 2A-C, 3A-F, 4A-D, 5A-B, and 6, foldable section 30 comprises exactly three subsections, in which case the foldable section may be considered a triple-collar section, and stent-graft 20 may be considered a triple-collar stent-graft. For other applications, foldable section 30 comprises more than three subsections, such as described hereinbelow with reference to FIG. 7. Stent-graft 20 is configured to assume a delivery configuration for endoluminal delivery, and a deployment configuration for deployment in a body lumen, such as a blood vessel.

When the stent-graft is in the deployment configuration, as show in FIG. 1, the stent-graft, including foldable section 30, is in a radially-expanded state, and the foldable section is in a longitudinally-folded state. In this folded state, second subsection 34 is radially sandwiched between first and third subsections 32 and 36. First subsection 32 is radially outward of second subsection 34, and third subsection 36 is radially inward of second subsection 34. As a result, second subsection 34 at least partially longitudinally overlaps with both first and third subsections 32 and 36. For some applications, as shown in FIG. 1, second subsection 34 entirely longitudinally overlaps with both first and third subsections 32 and 36.

First subsection 32 has first and second longitudinal edges 40 and 42. Second subsection 34 has third and fourth longitudinal edges 44 and 46. Third subsection 36 has fifth and sixth longitudinal edges 48 and 50. Second edge 42 joins third edge 44, defining a border therebetween, and fourth edge 46 joins fifth edge 48, defining a border therebetween.

Typically, when the stent-graft is in the deployment configuration, as shown in FIG. 1, fourth edge 46 of second subsection 34 is generally sandwiched between first edge 40 of first subsection 32 and fifth edge 48 of third subsection 36, such that first edge 40 is radially outward of fourth edge 46, and fifth edge 48 is radially inward of fourth edge 46. In addition, third edge 44 of second subsection 34 is generally sandwiched between second edge 42 of first subsection 32 and sixth edge 50 of third subsection 36, such that second edge 42 is radially outward of third edge 44, and sixth edge 50 is radially inward of third edge 44.

Figure 2A:
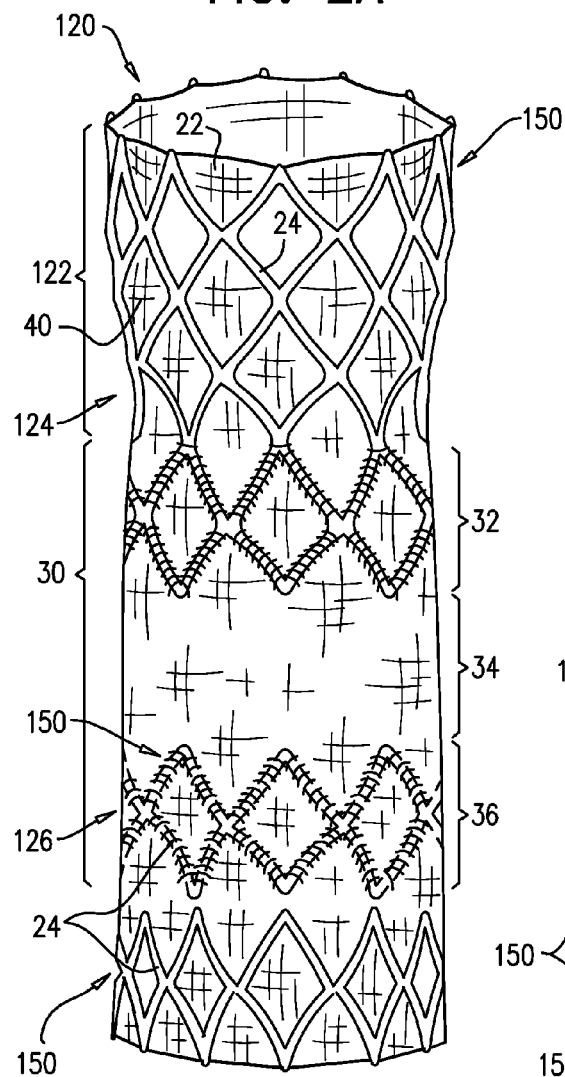
FIGS. 2A-B are schematic illustrations of an endovascular stent-graft, in accordance with an application of the present invention.
Figure 2B:
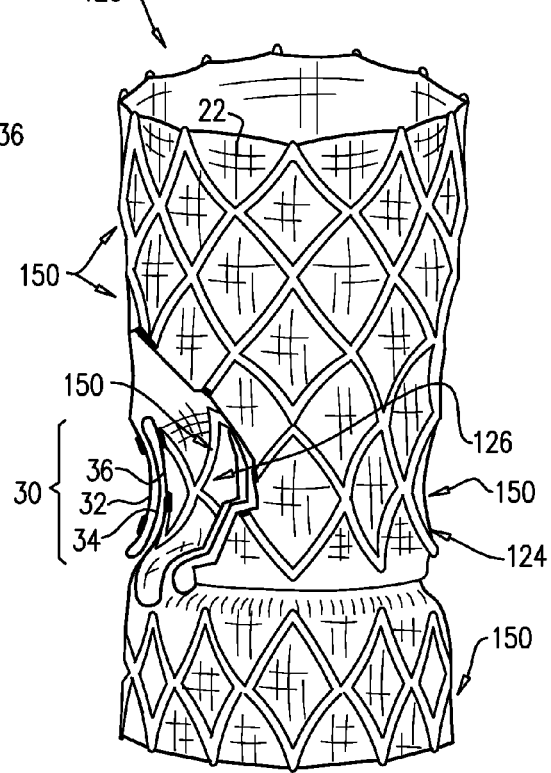

Reference is now made to FIGS. 2A-B, which are schematic illustrations of a stent-graft 120, in accordance with an application of the present invention. Stent-graft 120 is one configuration of the foldable endovascular stent-graft provided in applications of the present invention. Stent-graft 120 is shown in FIG. 2A a delivery configuration (except as noted below), in a longitudinally-expanded state, and in FIG. 2B in a deployment configuration. Like stent-graft 20, described hereinabove with reference to FIG. 1, and the other configurations of the foldable endovascular stent-graft provided in applications of the present invention, stent-graft 120 comprises foldable section 30. Unlike stent-graft 20, stent-graft 120 comprises a generally tubular proximal portion 122 that joins and extends distally from first edge 40 of first subsection 32, in a direction away from second subsection 34. Unless otherwise indicated or clearly not feasible, all of the features described with reference to stent-graft 20 may also be provided for stent-graft 120, and vice versa, as well as for the other configurations of the foldable stent-graft provided in applications of the present invention.

For clarity of illustration, in FIG. 2A stent-graft 120 is shown in a radially-expanded state. In actual use, stent-graft 120, including foldable section 30, is in a radially-compressed state when in the delivery configuration, such as shown in FIG. 3A (for stent-graft 220), FIG. 4A (for stent-graft 320), and/or FIG. 6 (for stent-graft 20, 120, 220, or 320).

When the stent-graft is in the delivery configuration, foldable section 30 is in a longitudinally-expanded state, in which state first and third subsections 32 and 36 longitudinally surround second subsection 34. Typically, first and third subsections 32 and 36 are longitudinally adjacent to second subsection 34, i.e., first and second subsections 32 and 34 are arranged longitudinally contiguously, and second and third subsections 34 and 36 are arranged longitudinally contiguously.

For some applications, as shown in FIGS. 1 and 2A-B, an average surface coverage ratio of structural stent elements 24 on fluid flow guide 22 along second subsection 34 is no more than 20%, such as no more than 10%, of the greater of (a) an average surface coverage ratio on fluid flow guide 22 along first subsection 32 and (b) an average surface coverage ratio on fluid flow guide 22 along third subsection 36. For some applications, none of structural stent elements 24 is disposed along second subsection 34. Providing this lower average surface coverage ratio (such as no surface coverage) provides greater evertibility to second subsection 34, thereby enabling the transition of foldable section 30 from the longitudinally-expanded state to the folded state. During this transition, the second subsection is everted, i.e., turned inside-out.

Alternatively or additionally, the average surface coverage ratio of structural stent elements 24 on fluid flow guide 22 along second subsection 34 is not necessarily no more than 20%. The greater evertibility of second subsection 34 compared to first and third subsections 32 and 36 may be provided by:
configuring the structural stent elements along the second subsection to be softer and/or thinner than the structural stent elements along the first and/or the third subsections; and/or
configuring the structural stent elements along the second subsection to be longitudinally short, e.g., as simple circles disposed circumferentially around the stent-graft. Optionally, the structural stent elements extend around less than 360 degrees of the circumference of the stent-graft, i.e., are circumferentially incomplete, in order to increase the evertibility of the second subsection.

For some applications, a first subgroup 124 of structural stent elements 24 is attached (e.g., sutured) to first subsection 32, and a second subgroup 126 of structural stent elements 24 is attached (e.g., sutured) to third subsection 36. For some applications, one of first and second subgroups 124 and 126 of structural stent elements 24 is attached (e.g., sutured) to an internal surface of fluid flow guide 22, and the other of first and second subgroups 124 and 126 is attached (e.g., sutured) to an external surface of fluid flow guide 22. For example, as shown in FIGS. 1 and 2A-B, first subgroup 124 may be attached to the external surface of first subsection 32, and second subgroup 126 may be attached to the internal surface of third subsection 36.

For some applications, as shown in FIGS. 1 and 2A-B, structural stent elements 24 are arranged as a plurality of generally circumferential bands 150. Longitudinal adjacent ones of bands 150 may or may not be joined to one another. For some applications, one or more of circumferential bands 150 is attached (e.g., sutured) to fluid flow guide 22 along first subsection 32 (either to an external surface and/or to an internal surface thereof), and one or more of circumferential bands 150 is attached (e.g., sutured) to fluid flow guide 22 along third subsection 36 (either to an external surface and/or to an internal surface thereof). Optionally, in addition, one or more of circumferential bands 150 is attached to fluid flow guide 22 along second subsection 34 (either to an external surface and/or to an internal surface thereof).

Alternatively, none of circumferential bands 150 is attached to fluid flow guide 22 along second subsection 34. The longitudinal end of the circumferential band attached (e.g., sutured) to the first subsection at second longitudinal edge 42 thereof thus may serve to define the border between the first and the second subsections. Similarly, the longitudinal end of the circumferential band attached (e.g., sutured) to the third subsection at fifth longitudinal edge 48 thereof thus may serve to define the border between the third and the second subsections. Foldable section 30 folds along these two borders.

For some applications, as shown in FIG. 2B, a first subgroup of structural stent elements 24, such as at least one (e.g., exactly one) of circumferential bands 150, is attached to fluid flow guide 22 along first subsection 32, and at least partially curves inwardly, when the foldable section is in the longitudinally-folded state. For example, the first subgroup may be concave in at least one direction (e.g., in a direction parallel to a central longitudinal axis of the stent-graft, as shown), as viewed from outside stent-graft 120. Alternatively, the first subgroup at least partially curves outwardly (e.g., may be convex) in a directional parallel to the central longitudinal axis of the stent-graft, as viewed from outside stent-graft 120 (configuration not shown). For some applications, an at least partially inwardly- or outwardly-curved portion of the first subgroup extends to second longitudinal edge 42 of first subsection 32, i.e., to the border between the first and the second subsections.

Alternatively or additionally, as shown in FIG. 2B, a second subgroup of structural stent elements 24, such as at least one (e.g., exactly one) of circumferential bands 150, is attached to fluid flow guide 22 along third subsection 36, and at least partially curves inwardly when the foldable section is in the longitudinally-folded state. For example, the second subgroup may be concave in at least one direction (e.g., in a direction parallel to a central longitudinal axis of the stent-graft, as shown), as viewed from outside stent-graft 120. Alternatively, the second subgroup at least partially curves outwardly (e.g., may be convex), in a directional parallel to the central longitudinal axis of the stent-graft), as viewed from outside stent-graft 120 (configuration not shown). For some applications, an at least partially inwardly- or outwardly-curved portion of the second subgroup extends to fifth longitudinal edge 48 of third subsection 36, i.e., to the border between the third and the second subsections.

The curved shapes of first and third subsections 32 and 36 generally correspond with each other, thereby interlocking, and thus axially mounting, these two subsections when the foldable section is folded. This interlocking reduces the likelihood of migration of the first subsection relative to the third subsection after implantation in the longitudinally-folded deployment state. Alternatively, the first and the second subgroups of the structural stent elements have respective non-curved shapes that generally correspond with each other, in order to provide the interlocking. As used in the present application, including in the claims, to "interlock," with respect to two elements, means to engage the two elements with each other by overlapping or by the fitting together of projections and recesses; the two elements need not come in physical contact with each other (e.g., the second subsection is sandwiched between the first and the third subsections when the foldable section is folded, such that the first and the third subsections do not generally come in contact with each other).

For some applications, structural stent elements 24 disposed along proximal portion 122 of stent-graft 120 do not curve inwardly.

For some applications, such as shown in FIG. 1, at least one (e.g., exactly one) of circumferential bands 150 is attached to fluid flow guide 22 along first subsection 32, and longitudinally protrudes beyond first longitudinal edge 40 of first subsection 32.

For some applications, as shown in FIG. 1, stent-graft 20 further comprises a plurality of circumferentially-disposed radiopaque markers 160. For some applications, the radiopaque markers are disposed at two or three of the following sets of locations: (1) a set of one or more locations near first edge 40 of first subsection 32, (2) a set of one or more locations near fourth edge 46 of second subsection 34, and (3) a set of one or more locations near fifth edge 48 of third subsection 36. For some of these applications, a first subset 162 of radiopaque markers 160 is coupled to structural stent elements 24 that are attached to fluid flow guide 22 along first subsection 32, and a second subset 164 of radiopaque markers 160 is coupled to structural stent elements 24 that are attached to fluid flow guide 22 along third subsection 36, as shown in FIG. 1.

During an implantation procedure, such as described hereinbelow with reference to FIGS. 3D-E, the surgeon may observe the relative longitudinal positions of first and second subsets 162 and 164 of radiopaque markers 160. The surgeon ascertains that foldable section 30 has fully assumed the longitudinally-folded state by observing that first and second subsets 162 and 164 are longitudinally aligned with each other.

For some applications, radiopaque markers 160 of first subset 162 are disposed with an angular (i.e., circumferential, rotational) offset with respect to radiopaque markers 160 of second subset 164, when the foldable section is in its delivery configuration. For example, the offset may be 0 degrees, or any other angular value. While folding the foldable section, the surgeon observes the relative rotational orientation of the radiopaque markers of the two subsets 162 and 164 of markers, and rotates a portion of the stent-graft appropriately in order to maintain rotational alignment between the first and the third subsections during folding of the foldable section.

Reference is made to FIG. 2C, which is a schematic illustrations of another stent-graft 180, in accordance with an application of the present invention. Stent-graft 180 is one configuration of the foldable endovascular stent-graft provided in applications of the present invention. Stent-graft 180 is shown in FIG. 2C in a delivery configuration, in a longitudinally-expanded state. Like stent-grafts 20 and 120, described hereinabove with reference to FIGS. 1 and 2A-B, and the other configurations of the foldable endovascular stent-graft provided in applications of the present invention, stent-graft 180 comprises foldable section 30. Unless otherwise indicated or clearly not feasible, all of the features described with reference to stent-grafts 20 and 120 may also be provided for stent-graft 180, and vice versa, as well as for the other configurations of the foldable stent-graft provided in applications of the present invention.

For some applications, one 181 of circumferential bands 150 includes first portions 183 and second portions 182. When foldable section 30 is in its longitudinally-expanded state, first portions 183 are disposed along at least a portion of first subsection 32, and second portions 182 are disposed along a portion of second subsection 34, i.e., circumferential band 181 longitudinally spans the border between the first and the second subsections. First portions 183 are at least partially attached (e.g., sutured) to fluid flow guide 22 along first subsection 32. Second portions 182 are not attached (e.g., are not sutured) to fluid flow guide 22. As a result, when foldable section 30 assumes its longitudinally-folded state, unattached portions 182 extend beyond second longitudinal edge 42 of first subsection 32 and third longitudinal edge 44 of second subsection 34, because the foldable section folds longitudinally along the border between second longitudinal edge 42 and third longitudinal edge 44.

Alternatively or additionally, for some applications, one 186 of circumferential bands 150 includes first portions 185 and second portions 184. When foldable section 30 is in its longitudinally-expanded state, first portions 185 are disposed along at least a portion of third subsection 36, and second portions 184 are disposed along a portion of second subsection 34, i.e., circumferential band 181 longitudinally spans the border between the third and second subsections. First portions 185 are at least partially attached (e.g., sutured) to fluid flow guide 22 along third subsection 36. Second portions 182 are not attached (e.g., are not sutured) to fluid flow guide 22. As a result, when foldable section 30 assumes its longitudinally-folded state, unattached portions 184 extend beyond fourth longitudinal edge 46 of second subsection 34 and fifth longitudinal edge 48 of third subsection 36, because the foldable section folds longitudinally along the border between fourth longitudinal edge 46 and fifth longitudinal edge 48.

Reference is now made to FIGS. 3A-F, which are schematic illustrations of an exemplary method of deploying a stent-graft 220 in the vicinity of an sub-renal abdominal aortic aneurysm 260 of an abdominal aorta 62, in accordance with an application of the present invention. Stent-graft 220 is one configuration of the foldable endovascular stent-graft provided in applications of the present invention. Stent-graft 220 comprises foldable section 30, and is generally similar to stent-graft 20, described hereinabove with reference to FIG. 1, stent-graft 120, described hereinabove with reference to FIGS. 2A-B, and/or stent-graft 180, described hereinabove with reference to FIG. 2C, and may incorporate some or all the features of stent-graft 20, stent-graft 120, and/or stent-graft 180. For clarity of illustration, structural stent elements 24 are not shown on the deployed portion of stent-graft 220. Elements 24 may be attached to either an internal or an external surface of stent-graft 220, or a combination of the internal and external surfaces, such as described hereinabove with reference to FIGS. 1 and 2A-B.

As shown in FIG. 3A, during a first stage of the implantation procedure, stent-graft 220 is deployed using an endovascular stent delivery tool 270, which typically comprises a delivery catheter 272, a distal tip 274, and a guidewire 276. Stent-graft 220 is initially positioned in delivery catheter 272, restrained in the stent-graft's delivery configuration by the catheter. Stent-graft 220 is transvascularly (typically percutaneously) introduced into aorta 262, e.g., via one of the iliac arteries, while positioned in delivery catheter 272. In this exemplary deployment, delivery catheter 272 and distal tip 274 are advanced over guidewire 276 until the distal tip is positioned at or slightly above renal arteries 278A and 278B.

Figure 3B:
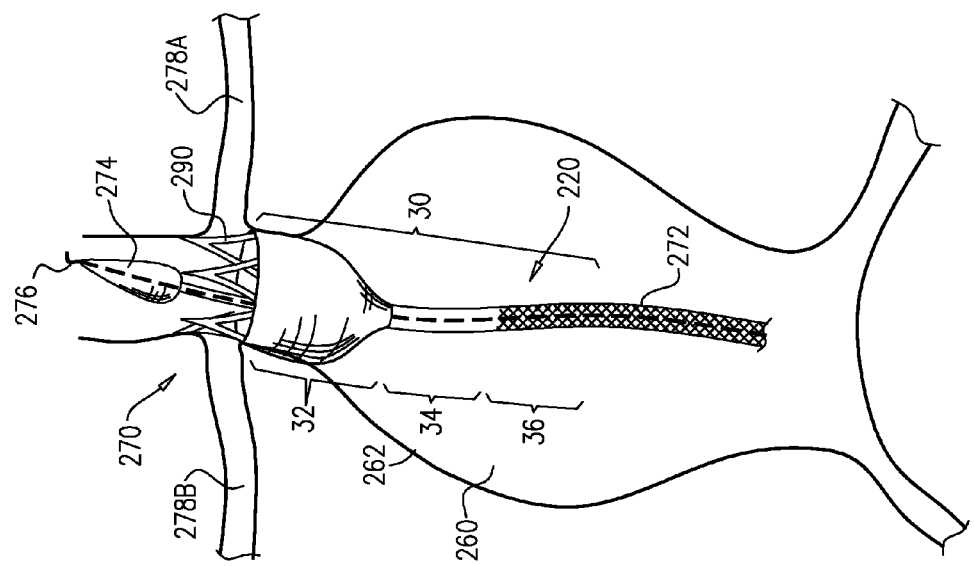
Figure 3A:
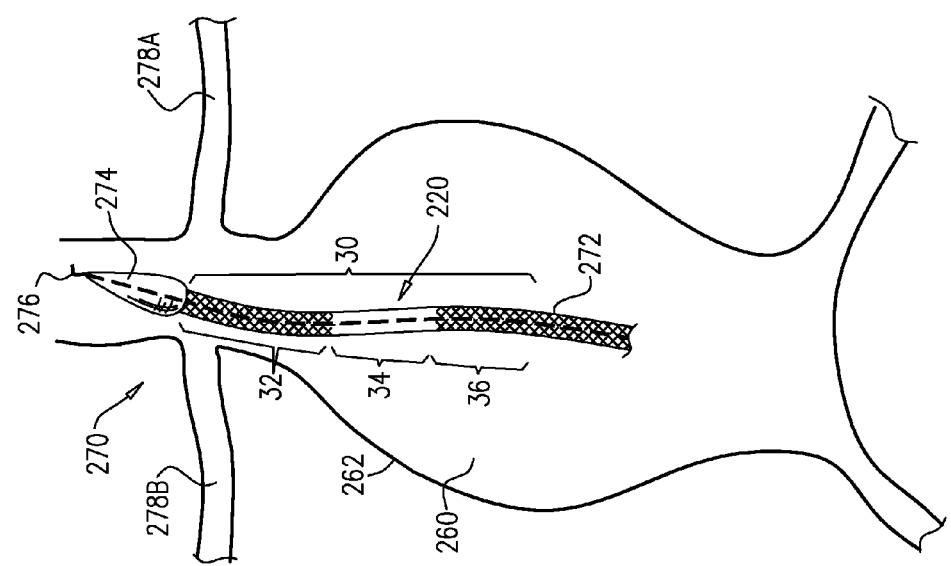

As shown in FIG. 3B, delivery catheter 272 is proximally withdrawn, releasing first subsection 32 of foldable section 30 in aorta 262. First subsection 32 radially expands as it is released, until it comes in contact with a wall of the blood vessel, e.g., a sub-renal neck 280 of aneurysm 260 in this exemplary deployment.

Figure 3C:
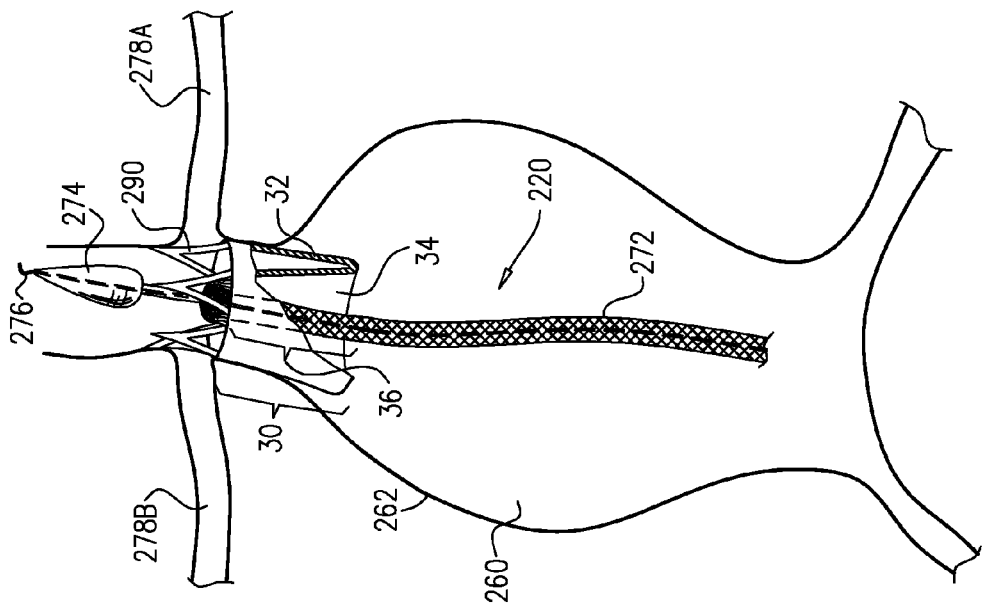

As shown in FIG. 3C, delivery catheter 272 is further proximally withdrawn, releasing second subsection 34 of foldable section 30 in aorta 262. Second subsection 34 radially expands as it is released.

Figure 3D:
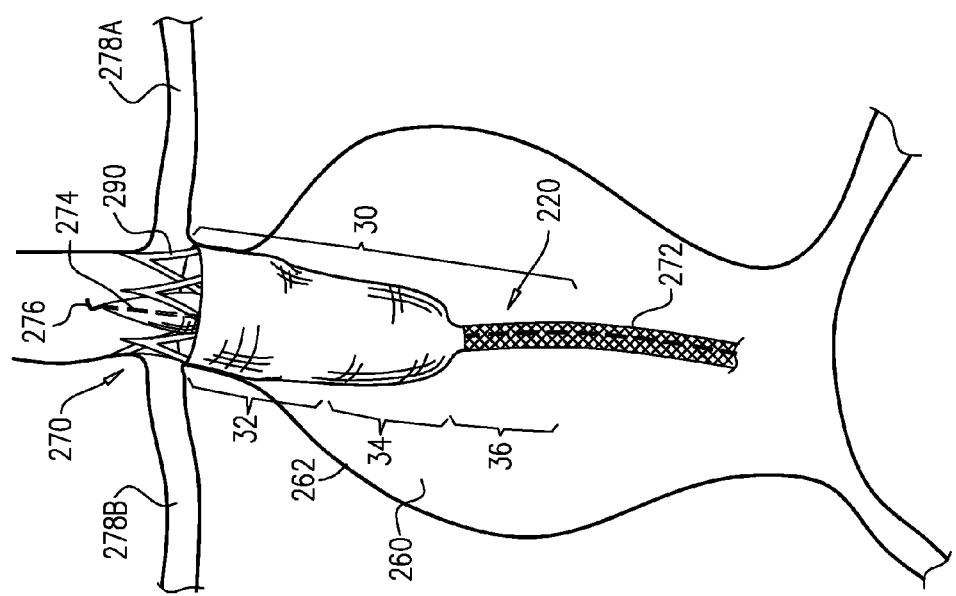

As shown in FIG. 3D, the surgeon begins folding foldable section 30 of stent-graft 220. The surgeon distally advances delivery catheter 272, thereby folding second subsection 34 within first subsection 32. As a result, first and second subsections 32 and 34 longitudinally overlap.

As shown in FIG. 3E, the surgeon further proximally withdraws delivery catheter 272, thereby releasing third subsection 36 within both first and second subsections 32 and 34. Third subsection 36 radially expands as it is released from the catheter, thereby completing the transition of foldable section 30 to its longitudinally-folded state, such that second subsection 34 is radially sandwiched between first and third subsections 32 and 36. In FIG. 3E, a portion 282 of stent-graft 220 proximal and adjacent to foldable section 30 is also shown partially deployed from delivery catheter 272. The remainder of stent-graft 220 is still positioned in catheter 272.

FIG. 3F shows stent-graft 220 after the stent-graft has fully assumed the deployment configuration, and delivery tool 270 has been withdrawn from aorta 262. The folding of foldable section 30 thickens the graft material of fluid flow guide 22, thereby providing improved sealing between the stent-graft and sub-renal neck 280 of aneurysm 260. Such improved sealing reduces the risk of type I endoleak, and/or provides improved structural support and/or resistance to fractures.

For some applications, as shown in FIGS. 3B-F, stent-graft 220 comprises distal anchoring elements 290, for example as described in PCT Publication WO 2010/150208, which is incorporated herein by reference, mutatis mutandis, e.g., with reference to FIGS. 3, 7A-C, 9A-B, 10A-B, 13, 15A-C, 16, 17, 18, 19, 20A-B, and/or 21A-B thereof.

Reference is now made to FIGS. 4A-D, which are schematic illustrations of an exemplary method of deploying first and second stent-grafts 320 and 322, in accordance with an application of the present invention. First stent-graft 320 is one configuration of the foldable endovascular stent-graft provided in applications of the present invention. First stent-graft 320 comprises foldable section 30, and is generally similar to stent-graft 20, described hereinabove with reference to FIG. 1, stent-graft 120, described hereinabove with reference to FIGS. 2A-B, stent-graft 180, described hereinabove with reference to FIG. 2C, and/or stent-graft 220, described hereinabove with reference to FIGS. 3A-F, and may incorporate some or all the features of stent-graft 20, stent-graft 120, stent-graft 180, and/or stent-graft 220. Second stent-graft 322 is shaped so as to define a side-facing fenestration 324. Second stent-graft 322 may be a conventional stent-graft, or may implement some of the techniques described in the applications incorporated hereinbelow by reference. Optionally, stent-graft 322 comprises a foldable section (configuration not shown).

Figure 4B:
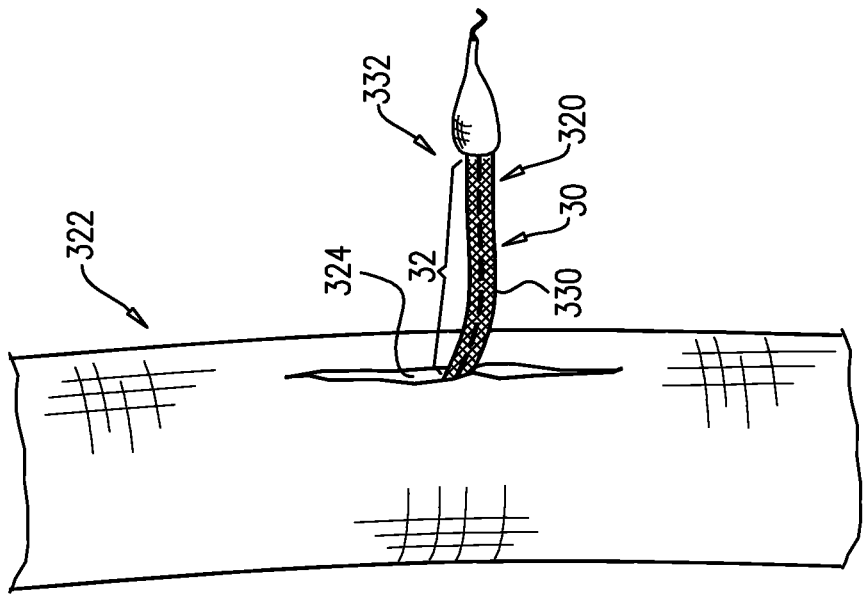
FIGS. 4A-D are schematic illustrations of an exemplary method of deploying first and second stent-grafts, in accordance with an application of the present invention.
Figure 4A:
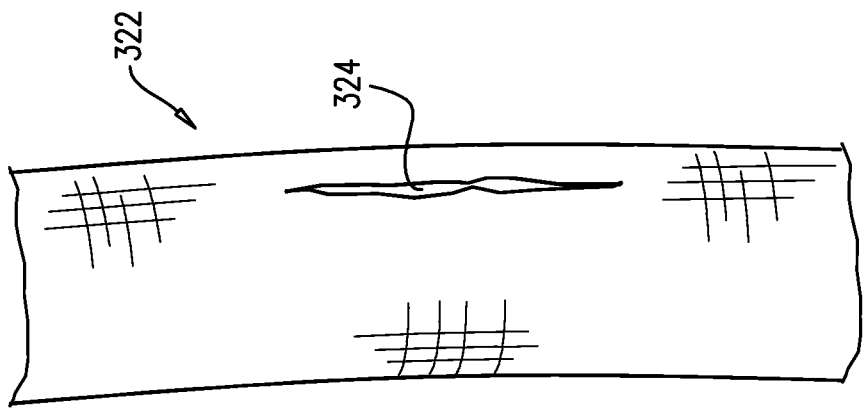

As shown in FIG. 4A, second stent-graft 322 is deployed in a blood vessel of human subject (for clarity of illustration, the anatomy is not shown). Second stent-graft 322 assumes a radially-expanded state.

As shown in FIG. 4B, first stent-graft 320, while in the deployment configuration in a delivery catheter 330 of a delivery tool 332, is passed partially through side-facing fenestration 324 of second stent-graft 322. The catheter is typically first introduced into second-stent graft 322, and then advanced through the fenestration and partially out of the second stent-graft, typically into a blood vessel that branches from the blood vessel in which the second stent-graft is positioned.

Figure 4D:
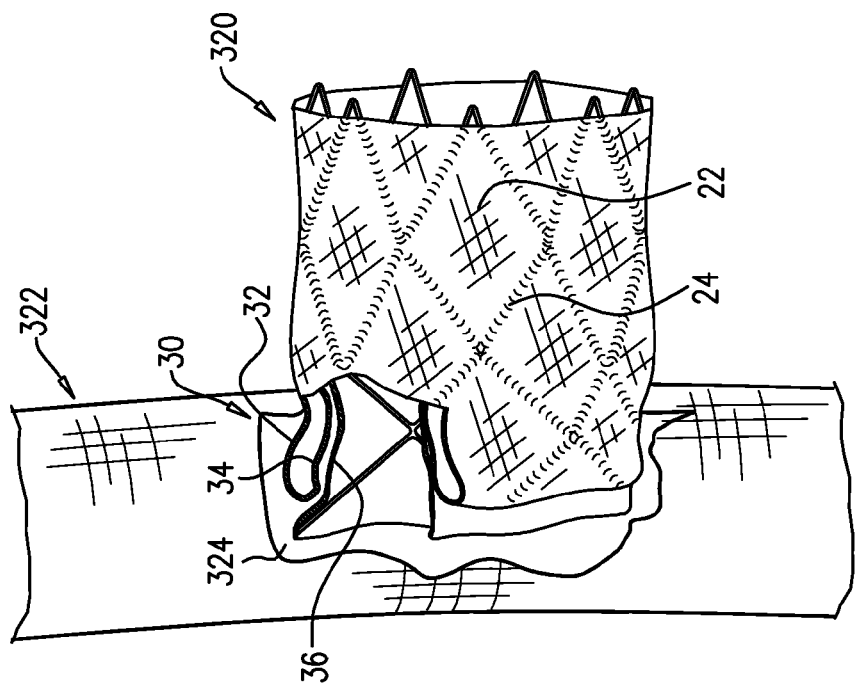
Figure 4C:
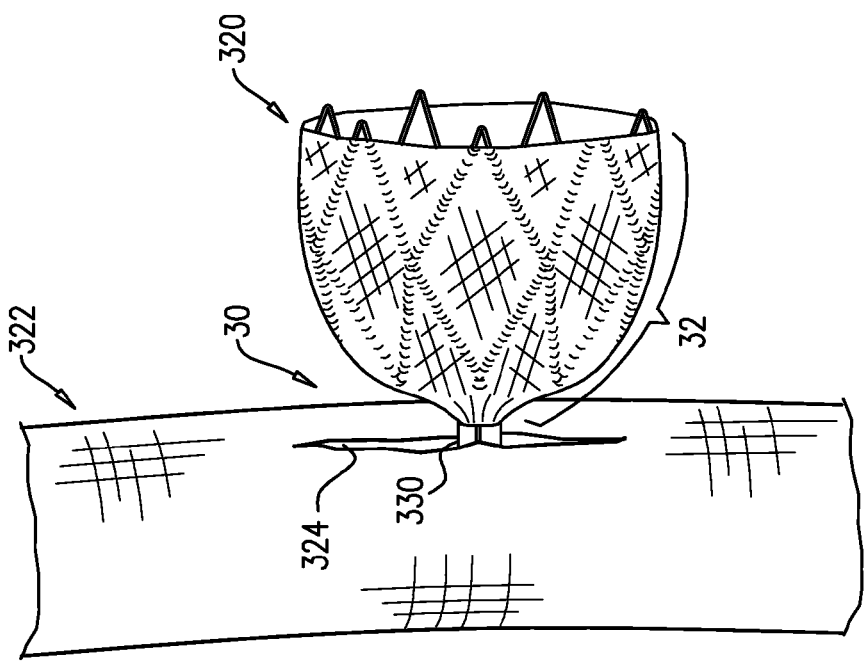

As shown in FIG. 4C, delivery catheter 330 is proximally withdrawn, releasing first subsection 32 of foldable section 30. First subsection 32 radially expands as it is released.

The surgeon folds foldable section 30 of stent-graft 320, by:

proximally withdrawing delivery catheter 330, thereby releasing second subsection 34 of foldable section 30, which radially expands, thereafter, distally advancing delivery catheter 330 further through fenestration 324, thereby folding second subsection 34 within first subsection 32, such that first and second subsections 32 and 34 longitudinally overlap, and thereafter, further proximally withdrawing delivery catheter 330, thereby releasing third subsection 36 within both first and second subsections 32 an 34.

Although these folding steps are not illustrated in FIGS. 4A-D, these steps are illustrated, mutatis mutandis, in FIGS. 3C-E, as described hereinabove.

The result of performing these steps is shown in FIG. 4D: foldable section 30 is in its longitudinally-folded state, such that second subsection 34 is radially sandwiched between first and third subsections 32 and 36. (In FIG. 4D, fluid flow guide 22 is shown partially cut-away around fenestration 324, to allow foldable section 30 to be seen). Foldable section 30 of first stent-graft 320 is dimensioned to be fixed to side-facing fenestration 324, when second stent-graft 322 is in a radially-expanded state and foldable section 30 is in its longitudinally-folded state. The folding of foldable section 30 thickens the graft material of fluid flow guide 22, thereby providing improved sealing between first stent-graft 320 and fenestration 324. In addition, the folding typically doubles or triples the number of structural support elements 24 along foldable section 30, thereby providing improved structural support at the junction between the first and the second stent-grafts.

The techniques described with reference to FIGS. 4A-D may be used, for example, to deploy:

second stent-graft 322 in the descending aorta in the vicinity of the renal arteries, and first stent-graft 320 in one of the renal arteries;

second stent-graft 322 in the aortic arch, and first stent-graft 320 in one of a brachiocephalic artery, a left common carotid artery, and a left subclavian artery; or second stent-graft 322 in the left and right iliac arteries, and first stent-graft 320 in the descending aorta.

For some applications, the techniques described with reference to FIGS. 4A-D are implemented in combination with techniques described in PCT Publication WO 2011/007354 and/or in PCT Publication 2011/064782, mutatis mutandis, both of which are incorporated herein by reference.

Figure 5A:
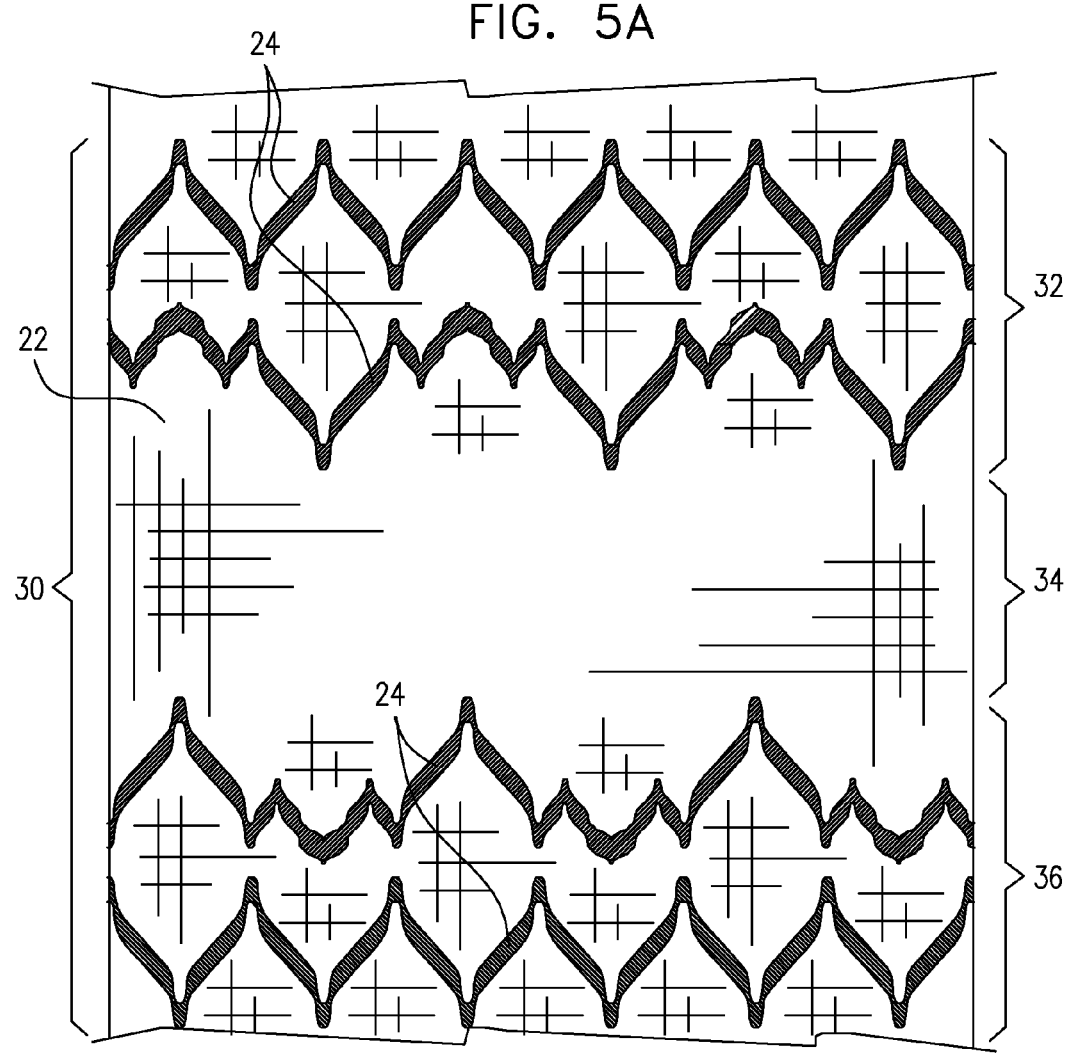

Reference is now made to FIGS. 5A and 5B, which are exemplary stent patterns, in accordance with respective applications of the present invention. These figures show foldable section 30 cut open along a line parallel to the longitudinal axis of the stent-graft and laid straight. The foldable section is shown in its longitudinally-expanded delivery configuration. Although stent elements 24 are shown attached to the same surface of fluid flow guide 22, alternatively a portion of the stent elements is attached to an external surface of the fluid flow guide, and another portion is attached an internal surface of the fluid flow guide, as described hereinabove, such as with reference to FIGS. 1 and/or 2A-B.

Reference is now made to FIG. 6, which is a schematic cross-sectional illustration of an elongated delivery tool 400, in accordance with an application of the present invention. Elongated delivery tool 400 may be used to deliver and deploy stent-graft 20, stent-graft 120, stent-graft 180, stent-graft 220, and/or first stent-graft 320. For example, elongated delivery tool 400 may serve as delivery tool 270, described hereinabove with reference to FIGS. 3A-F, and/or delivery tool 332, described hereinabove with reference to FIGS. 4A-D.

Delivery tool 400 comprises a tubular external shaft 410, and an internal shaft 412, which is slidably disposed within external shaft 410. Typically, internal shaft 412 is shaped so as to define a lumen 414 therethrough, in which a guidewire 416 may be slidably positioned (for clarity of illustration, the guidewire is not shown in FIG. 6). A distal tip 416 may be coupled to a distal end of internal shaft 410. External shaft 410 typically has a diameter of no more than 28 Fr, such as no more than 22 Fr, e.g., no more than 14 Fr.

Stent-graft 20, 120, 180, 220, or 320 is initially disposed, while longitudinally stretched out in the delivery configuration, between external and internal shafts 410 and 412 of delivery tool 400, in a vicinity of a distal end 418 of external shaft 412.

For some applications, delivery tool 400 further comprises a stopper member 420 fixed to internal shaft 412, which is initially disposed proximally adjacent the stent-graft, thereby preventing proximal movement of the stent-graft inside the delivery tool when external shaft 410 is withdrawn proximally relative to internal shaft 414.

Reference is now made to FIG. 7, which is a schematic cross-sectional illustration of one wall of a doubled foldable section 530, in accordance with an application of the present invention. This configuration may be used in combination with any of the configuration of the foldable endovascular stent-graft described herein.

Doubled foldable section 530 comprises first and second foldable sections 30A and 30B, each of which, if taken individually, is generally similar to foldable section 30, described hereinabove. A third subsection 36A of first foldable section 30A serves also as a first subsection 32B of second foldable section 30B. As a result, first foldable section 30A partially longitudinally overlaps second foldable section 30B when the stent-graft is in the deployment configuration. When the stent-graft is in the deployment configuration, this configuration provides even greater thickening of the foldable section and even greater increased structural support, than the configuration of foldable section 30 described hereinabove.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

U.S. Provisional Application 60/991,726, filed Dec. 2, 2007

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208

PCT Application PCT/IL2010/000564, filed Jul. 14, 2010, which published as PCT Publication WO 2011/007354

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2011/000135, filed Feb. 8, 2011, entitled, "Thermal energy application for prevention and management of endoleaks in stent-grafts," which published as PCT Publication WO 2011/095979

U.S. application Ser. No. 13/031,871, filed Feb. 22, 2011, entitled, "Flexible stent-grafts," which published as US Patent Application Publication 2011/0208289

U.S. Provisional Application 61/496,613, filed Jun. 14, 2011

U.S. Provisional Application 61/505,132, filed Jul. 7, 2011

U.S. Provisional Application 61/529,931, filed Sep. 1, 2011

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
    an endovascular stent-graft, which comprises: (a) a fluid flow guide; and (b) a plurality of structural stent elements attached to at least a portion of the fluid flow guide; and
    an elongated delivery tool, wherein the stent-graft is configured (a) to define a generally tubular foldable section, which comprises first, second, and third subsections, and (b) to assume:

a delivery configuration, when disposed in the elongated delivery tool, in which delivery configuration (a) the stent-graft, including the foldable section, is in a radially-compressed state, and (b) the foldable section is in a longitudinally-expanded state, in which state the first and the third subsections longitudinally surround the second subsection, and a deployment configuration, in which (a) the stent-graft, including the foldable section, is in a radially-expanded state, and (b) the foldable section is in a longitudinally-folded state, such that the second subsection is radially sandwiched between the first and the third subsections.

2. The apparatus according to claim 1, wherein an average surface coverage ratio of the structural stent elements on the fluid flow guide along the second subsection is no more than 20% of the greater of (a) an average surface coverage ratio of the structural stent elements of the fluid flow guide along the first subsection and (b) an average surface coverage ratio of the structural stent elements on the fluid flow guide along the third subsection.

3. The apparatus according to claim 1,
wherein a first subgroup of the structural stent elements is attached to the first subsection, and a second subgroup of the structural stent elements is attached to the third subsection, and
wherein one of the first and the second subgroups of the structural stent elements is attached to an internal surface of the fluid flow guide, and the other of the first and the second subgroups is attached to an external surface of the fluid flow guide.

4. The apparatus according to claim 1, wherein, when the stent-graft is in the delivery configuration, the first and the second subsections are arranged longitudinally contiguously, and the second and the third subsections are arranged longitudinally contiguously.

5. The apparatus according to claim 1, wherein a first subgroup of the structural stent elements are attached to the fluid flow guide along the first subsection, and at least partially curves inwardly, when the foldable section is in the longitudinally-folded state.

6. The apparatus according to claim 1, wherein a second subgroup of the structural stent elements are attached to the fluid flow guide along the third subsection, and at least partially curves inwardly, when the foldable section is in the longitudinally-folded state.

7. The apparatus according to claim 1, wherein first and second subgroups of the structural stent elements are attached to the fluid flow guide along the first and the third subsections, respectively, and wherein the first and the second subgroups are shaped to interlock the first and the third subsections when the foldable section is in the longitudinally-folded state.

8. The apparatus according to claim 1,
wherein the stent-graft is a first stent-graft,
wherein the apparatus further comprises a second stent-graft, which is shaped so as to define a side-facing fenestration, and
wherein the foldable section of the first stent-graft is dimensioned to be fixed to the side-facing fenestration, when the second stent-graft is in a radially-expanded state and the foldable section is in the longitudinally-folded state.

9. The apparatus according to claim 1, wherein the stent-graft further comprises a plurality of circumferentially-disposed radiopaque markers.

10. The apparatus according to claim 9,
wherein the first subsection has first and second longitudinal edges,
wherein the second subsection has third and fourth longitudinal edges,
wherein the third subsection has fifth and sixth longitudinal edges,
wherein the second edge joins the third edge,
wherein the fourth edge joins the fifth edge, and
wherein a first subset of the radiopaque markers are disposed near the first edge of the first subsection, and a second subset of the radiopaque markers are disposed near the fifth edge of the third subsection.

11. The apparatus according to claim 1, wherein the elongated delivery tool comprises:
a tubular external shaft; and
an internal shaft, which is slidably disposed within the external shaft,
wherein the stent-graft is initially disposed, in the delivery configuration, between the external and the internal shafts of the delivery tool, in a vicinity of a distal end of the external shaft.

12. The apparatus according to claim 11, wherein the delivery tool further comprises a stopper member fixed to the internal shaft, which is initially disposed proximally adjacent the stent-graft, thereby preventing proximal movement of the stent-graft inside the delivery tool when the external shaft is withdrawn proximally relative to the internal shaft.

13. The apparatus according to claim 1, wherein the foldable section is configured, when in the longitudinally-folded state, to provide blood-flow sealing between the longitudinally-folded foldable section and a wall of a blood vessel, so as to reduce a risk of type I endoleak.

14. A method comprising:
providing an endovascular stent-graft, which includes a fluid flow guide, and a plurality of structural stent elements attached to at least a portion of the fluid flow guide, wherein the stent-graft is configured to define a generally tubular foldable section, which comprises first, second, and third subsections;
transvascularly introducing the stent-graft into a blood vessel of a human subject while the stent-graft is disposed in an elongated delivery tool in a delivery configuration, in which (a) the stent-graft, including the foldable section, is in a radially-compressed state, and (b) the foldable section is in a longitudinally-expanded state, in which state the first and the third subsections longitudinally surround the second subsection; and
thereafter, transitioning the stent-graft to a deployment configuration in the blood vessel, in which configuration (a) the stent-graft, including the foldable section, is in a radially-expanded state, and (b) the foldable section is in a longitudinally-folded state, such that the second subsection is radially sandwiched between the first and the third subsections.

15. The method according to claim 14, wherein providing the stent-graft comprises providing the stent-graft in which an average surface coverage ratio of the structural stent elements of the structural stent elements on the fluid flow guide along the second subsection is no more than 20% of the greater of (a) an average surface coverage ratio of the structural stent elements on the fluid flow guide along the first subsection and (b) an average surface coverage ratio of the structural stent elements on the fluid flow guide along the third subsection.

16. The method according to claim 14, wherein providing the stent-graft comprises providing the stent-graft in which: a first subgroup of the structural stent elements is attached to the first subsection, a second subgroup of the structural stent elements is attached to the third subsection, one of the first and the second subgroups of the structural stent elements is attached to an internal surface of the fluid flow guide, and the other of the first and the second subgroups is attached to an external surface of the fluid flow guide.

17. The method according to claim 14, wherein transitioning comprises transitioning the stent-graft to the deployment configuration in which the first and the second subsections are arranged longitudinally contiguously, and the second and the third subsections are arranged longitudinally contiguously.

18. The method according to claim 14, wherein providing the stent-graft comprises providing the stent-graft in which a first subgroup of the structural stent elements are attached to the fluid flow guide along the first subsection, and at least partially curves inwardly, when the foldable section is in the longitudinally-folded state.

19. The method according to claim 14, wherein providing the stent-graft comprises providing the stent-graft in which a second subgroup of the structural stent elements are attached to the fluid flow guide along the third subsection, and at least partially curves inwardly, when the foldable section is in the longitudinally-folded state.

20. The method according to claim 14, wherein providing the stent-graft comprises providing the stent-graft in which first and second subgroups of the structural stent elements are attached to the fluid flow guide along the first and the third subsections, respectively, and wherein transitioning the stent-graft to the deployment configuration comprises interlocking the first and the third subsections.

21. The method according to claim 14, wherein the stent-graft is a first stent-graft, and wherein the method further comprises:
   providing a second stent-graft, which is shaped so as to define a side-facing fenestration;
   transvascularly introducing the second stent-graft into the subject; and
   positioning the foldable section of the first stent-graft inside the side-facing fenestration,
   wherein transitioning comprises transitioning the first stent-graft to the deployment configuration while positioned in the side-facing fenestration, thereby fixing the first stent-graft to the side-facing fenestration.

22. The method according to claim 14, wherein providing the stent-graft comprises providing the stent-graft in which the stent-graft further includes a plurality of circumferentially-disposed radiopaque markers.

23. The method according to claim 22,
   wherein the first subsection has first and second longitudinal edges,
   wherein the second subsection has third and fourth longitudinal edges,
   wherein the third subsection has fifth and sixth longitudinal edges,
   wherein the second edge joins the third edge,
   wherein the fourth edge joins the fifth edge,
   wherein providing the stent-graft comprises providing the stent-graft in which a first subset of the radiopaque markers are disposed near the first edge of the first subsection, and a second subset of radiopaque markers are disposed near the fifth edge of the third subsection, and
   wherein transitioning the stent to the deployment configuration comprises ascertaining that the foldable section has fully assumed the longitudinally-folded state by observing that the first and the second subsets of the radiopaque markers are longitudinally aligned with each other.

24. The method according to claim 14, wherein transvascularly introducing comprises transvascular introducing the stent-graft into the blood vessel while the stent-graft is initially disposed, in the delivery configuration, between a tubular external shaft and an internal shafts of the elongated delivery tool, in a vicinity of a distal end of the external shaft.

25. The method according to claim 24,
   wherein the delivery tool further includes a stopper member fixed to the internal shaft,
   wherein transvascularly introducing comprises transvascularly introducing the stent-graft while the stopper member is initially disposed proximally adjacent the stent-graft, and
   wherein transitioning the stent-graft to the deployment configuration comprises withdrawing the external shaft proximally relative to the internal shaft, such that the stopper member prevents proximal movement of the stent-graft inside the delivery tool.

26. The method according to claim 14, wherein transitioning the stent-graft to the deployment configuration in the blood vessel comprises providing blood-flow sealing between the longitudinally-folded foldable section and a wall of the blood vessel, so as to reduce a risk of type I endoleak.

* * * * *